United States Patent
Sun et al.

(10) Patent No.: US 9,084,755 B2
(45) Date of Patent: Jul. 21, 2015

(54) METHOD FOR EXTRACTING AND SEPARATING GINKGOLIDES

(71) Applicant: CHENGDU BAIYU TECHNOLOGY PHARMACY CO., LTD, Chengdu, Sichuan (CN)

(72) Inventors: Yi Sun, Fushun (CN); Yonghong Zhu, Chengdu (CN); Zhengbing Tong, Wupao Town (CN); Jie Wang, Nanchong (CN)

(73) Assignee: CHENGDU BAIYU TECHNOLOGY PHARMACY CO., LTD., Sichuan (CN)

( * ) Notice: Subject to any disclaimer, the term of this patent is extended or adjusted under 35 U.S.C. 154(b) by 0 days.

(21) Appl. No.: 14/522,116

(22) Filed: Oct. 23, 2014

(65) Prior Publication Data

US 2015/0044311 A1  Feb. 12, 2015

Related U.S. Application Data

(63) Continuation of application No. PCT/CN2012/075633, filed on May 17, 2012.

(30) Foreign Application Priority Data

Apr. 23, 2012 (CN) .......................... 2012 1 0121252

(51) Int. Cl.
- *A61K 36/16* (2006.01)
- *C07D 493/20* (2006.01)
- *C07D 493/22* (2006.01)

(52) U.S. Cl.
CPC .............. *A61K 36/16* (2013.01); *C07D 493/20* (2013.01); *C07D 493/22* (2013.01); *A61K 2236/00* (2013.01); *A61K 2236/30* (2013.01)

(58) Field of Classification Search
None
See application file for complete search history.

(56) References Cited

U.S. PATENT DOCUMENTS

| 5,089,636 A | * | 2/1992 | Kwak et al. | 549/297 |
| 5,512,286 A | * | 4/1996 | Schwabe | 424/752 |

FOREIGN PATENT DOCUMENTS

| CN | 1491950 A | | 4/2004 |
| CN | 1594319 A | | 3/2005 |
| CN | 1686317 A | | 10/2005 |
| CN | 1733768 A | | 2/2006 |
| CN | 101054384 A | | 10/2007 |
| CN | 101134758 A | | 3/2008 |
| CN | 101392000 A | * | 3/2009 |
| CN | 101468997 A | * | 7/2009 |
| CN | 101773528 A | | 7/2010 |
| DE | 176708 C | | 10/1906 |
| DE | 2117429 A1 | | 10/1972 |
| EP | 0402925 A2 | | 12/1990 |

OTHER PUBLICATIONS

Jan. 24, 2013 International Search Report issued in International Application No. PCT/CN2012/075633.

Du Anquan et al., "Isolation and Identification of Ginkgolide A, B, C and Bilobalide from EGb", Anhui Research Institute of Medical Sciences, Hefei 230061, 2001.

Science and Technology Innovation Herald Article published 2011, vol. 25, p. 9.

* cited by examiner

*Primary Examiner* — Susan Hoffman
(74) *Attorney, Agent, or Firm* — Oliff PLC

(57) ABSTRACT

A method for extracting and separating ginkgolides. The ginkgolides obtained through steps of extraction on a ginkgo leaf, further extraction, column chromatography, crystallization, and crystal mixing comprise 25.0% to 50.0% of bilobalide ($C_{15}H_{18}O_8$), 20.0% to 45.0% of ginkgolide A ($C_{20}H_{24}O_9$), 10.0% to 30.0% of ginkgolide B ($C_{20}H_{24}O_{10}$), and 5.0% to 15.0% of ginkgolide C ($C_{20}H_{24}O_{11}$). The total quantity of the bilobalide, the ginkgolide A, the ginkgolide B, and the ginkgolide C is over 95%.

15 Claims, 4 Drawing Sheets

METHOD FOR EXTRACTING AND SEPARATING GINKGOLIDES

This is a Continuation of Application No. PCT/CN2012/075633 filed May 17, 2012, which claims the benefit of Chinese Application No. 201210121252.0 filed Apr. 23, 2012. The disclosure of the prior applications is hereby incorporated by reference herein in its entirety.

TECHNICAL FIELD

The present invention relates to the field of plant extraction, and particularly relates to a method for extracting and separating ginkgolides.

BACKGROUND

Since the 1960s of the last century, many countries have been researching chemical ingredients of ginkgo leaves by adopting a modern separation technology, and it is found that biological activities of multiple aspects of ginkgo leaves are related to the specific chemical ingredients contained in ginkgo leaves through pharmacologic experiments and clinical verifications. Dr. Willar Schwabe of Germany registered a simple extract of the ginkgo leaves for the first time, and applied for patents (W Schwabe DE176708 and DE2117429) in 1972, named EGb761, for treating cardiovascular and cerebrovascular diseases and nervous system diseases, with a remarkable therapeutic effect and without toxic side effects. Ginkgolids have a platelet-activating factor (PAF) antagonism. Ginkgo preparations are listed as therapeutic medications in Germany, France and China, other countries list Ginkgo preparations as health care foods or over-the-counter medications, and Ginkgo health care foods developed in the United States of America have been approved by FDA.

Ginkgolids belong to terpenoids, referred to as terpene lactones, consist of sesquiterpene lactone and diterpene lactone, and are one kind of important active ingredient in the ginkgo leaves. Bilobalide belongs to sesquiterpene lactone, was obtained through separation by R. T. Major in 1967 and K. Weinges in 1969, and is the only sesquiterpene lactone compound found in ginkgo leaves so far. Ginkgolids A, B, C, M and J are diterpene lactone compounds, were separated from ginkgo leaves by S. Furukawa in 1932 for the first time, and were further separated and the chemical structures thereof determined by K. Nakanish, M. Maruyama and K. Okabe in 1967. From a structural point of view, the molecular skeleton of bilobalides consists of 15 carbon atoms, has 4 five-membered rings, i.e. one five-membered carbon ring and three five-membered lactone rings, which are mutually condensed, wherein one tertiary butyl rare in a natural product is connected to the five-membered rings. The bilobalide is very strong in biological activity, has a function of promoting nerve growth, may prevent function change caused by oxidative stress of brain cell mitochondria, improve the memory function of old people, prevent senile dementia, and prevent brain and spinal cord nerve demyelination, and has stronger neurotrophy and neuroprotection than those of ginkgolides. Ginkgolide B has functions of resisting inflammation and shock, protecting heart and cerebral vessels, treating acute pancreatitis and the like. However, the molecular skeleton of ginkgolides consists of 20 carbon atoms, has 6 five-membered rings, i.e. 2 five-membered carbon rings, 3 five-membered lactone rings and 1 tetrahydrofuran ring, the two five-membered carbon rings are connected together in a volute form, and the left rings are connected in a condensing form to form a special rigid cage-shaped three-dimensional chemical structure. Ginkgolide molecules have tertiary butyls rare in a natural product. Ginkgolides comprise diterpene lactones and sesquiterpene lactones, the diterpene lactones mainly include ginkgolides A, B, C, J and M, and the sesquiterpene lactones include bilobalide.

After PAF was found in the early 70s of the 20th century, pharmacologists researched bilobalide, and confirmed that ginkgo terpene lactone is a platelet-activating factor antagonist and has a function of protecting the immune system, central nervous system and ischemia injury and a function of resisting shock, irritability and inflammation. Ginkgolides A, B, C, M and J are structurally different in the number of hydroxyls and positions of connecting the hydroxyls. Ginkgolides all are the platelet-activating factor antagonist, and a key ingredient of special physiological activity in ginkgo leaves.

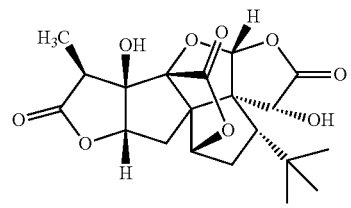

Structural formula of ginkgolide A, molecular formula: $C_{20}H_{24}O_9$, molecular weight: 408.4

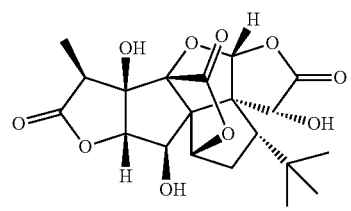

Structural formula of ginkgolide B, molecular formula: $C_{20}H_{24}O_{10}$, molecular weight: 424.4

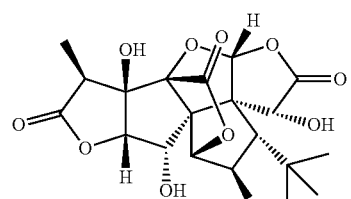

Structural formula of ginkgolide C, molecular formula: $C_{20}H_{24}O_{11}$, molecular weight: 440.4

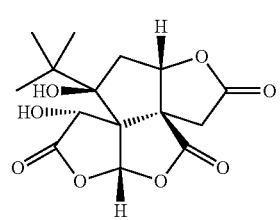

Structural formula of bilobalide, molecular formula: $C_{15}H_{18}O_8$, molecular weight: 326.3

Ginkgolides have a strong specificity inhibition function to a platelet-activating factor PAF receptor, wherein the PAF-resisting activity of ginkgolides is highest. The PAF is one kind of endogenous phospholipid generated by secretion of platelets and multiple kinds of inflamed tissues, is a most-effective platelet aggregation inducer found so far, and is closely related to generation and development of many diseases.

However, ginkgolides are regarded as a natural PAF receptor antagonist with the highest clinical application prospect, and its antagonistic activities are closely related to chemical structures. When R3 in a lactone structure is a hydroxyl or the number of hydroxyls is increased, the antagonistic activity to the PAF is weakened; and when R2 is a hydroxyl and R3 is H, the antagonistic activity is remarkably improved, wherein the antagonism of ginkgolide B to the PAF is strongest.

There are many methods for extracting and purifying ginkgolides, mainly including a solvent extraction method, a column extraction method, a solvent extraction-column extraction method, a supercritical extraction method and a chromatographic or column chromatographic purification method. These methods may not effectively separate high-content ginkgolides, and each composition proportion of ginkgolides is uncertain, therefore, pharmacological functions on the clinical use are different; and because ginkgolides are low in contents, and have certain safety risks, and no complete pharmacologic and toxicologic and clinical test data, the above methods all are in a testing stage and are not implemented in a pharmaceutical production process. Although there are relevant patents of ginkgolide injections in China, their compositions are different from those of the present invention; and through searching in multiple official websites in ICH member countries, no other ginkgolide injection products are available on the market so far. At present, ginkgolide ingredients are determined by mostly adopting an HPLC to UV method, an HPLC-MS method and an HPLC-ELSD method. These methods only determine the contents of each ingredient of ginkgolides, but do not actually reflect the quality characteristics of the drugs due to the absence of strict control on adverse reactive materials in the products, and thus fail to form a perfect drug quality control system. Although there are many patents for invention directed to ginkgolides, because the control methods are too simple and the composition proportions of the ginkgolides are uncertain, no traditional Chinese medicine injection can be made, and no clinical effect and application safety can be ensured.

Although there are many patents and reports about ginkgolides in China, Germany and other countries, the technological process, the quality control technology and the clinical applicability of the present invention are entirely different from those of other patents for invention, especially, the ingredients of terpene lactones obtained by different separation and purification processes are different. So far, no process reports of extracting a combination of effective parts of ginkgolides with a fixed proportion of four components (ginkgolides A, B and C and bilobalide) are available, nor are reports of fingerprint control technologies of four components in the ginkgolides and inspection methods of possibly remained macromolecules and proteins. The ginkgolide injection prepared by the present invention has obtained an approval number from the State Food and Drug Administration, with GYZZ of Z20110035, and is a first injection of effective parts of ginkgo in the world, and is distinct and clear in structure.

SUMMARY

The technical problem to be solved by the present invention is to provide a method for extracting and separating ginkgolides, wherein ginkgolides with fixed components can be obtained by adopting this method. According to an embodiment of the present invention, this method comprises the following steps:

A. extracting: crushing ginkgo leaves, adding an organic solvent for extraction, adding an anti-oxidization protection agent in a concentrated extracted solution, adjusting a pH value to 4 to 5 with a pH adjusting agent, concentrating, and refrigerating.

wherein, the organic solvent for extraction is ethanol, acetone or ethyl acetate, with a concentration of 50 to 80% v/v and an amount of 5 to 12 times, preferably 6 to 10 times.

According to an embodiment of the present invention, the extraction method is reflux extraction or decoction extraction.

1) Reflux Extraction:

ethanol: concentration 50 to 80% v/v, extraction temperature 75 to 85° C., extraction times 2 to 3 times with 1 to 2 h a time;

acetone: concentration 50 to 80% v/v, extraction temperature 45 to 55° C., extraction times 2 to 3 times with 1 to 2 h a time;

ethyl acetate: concentration 50 to 80% v/v, extraction temperature 55 to 65° C., extraction times 2 to 3 times with 1 to 2 h a time;

vacuum degree: −0.02 to 0.08 Mpa

According to an embodiment of the present invention, preferred extraction conditions: extraction is performed 3 times with 1.5 h a time; the concentration of the ethanol should preferably select 65% v/v; the concentration of the acetone should preferably select 50% v/v; and the concentration of the ethyl acetate should preferably select 60% v/v.

2) Decoction Extraction:

ethanol: concentration 50 to 80% v/v, extraction temperature 80 to 90° C., extraction times 2 to 3 times with 1 to 2 h a time;

acetone: concentration 50 to 80% v/v, extraction temperature 50 to 60° C., extraction times 2 to 3 times with 1 to 2 h a time;

ethyl acetate: concentration 50 to 80% v/v, extraction temperature 60 to 65° C., extraction times 2 to 3 times with 1 to 2 h a time;

According to an embodiment of the present invention, preferred extraction conditions: extraction is performed 3 times with 1.5 h a time; the concentration of the ethanol should preferably select 65% v/v; the concentration of the acetone should preferably select 50% v/v; and the concentration of the ethyl acetate should preferably select 60% v/v.

After an extracted solution is heated in a concentrating process, ginkgolides are easily decomposed, and it requires adding a protection agent and a pH adjusting agent. Adding the protection agent is to prevent the ginkgolides from being decomposed through oxidization when being heated, and available anti-oxidization protection agents mainly include neutral amino acids comprising at least one of serine, methionine, asparagine and threonine, preferably methionine.

The pH adjusting agent is mainly an organic weak acid including at least one of citric acid, malic acid and sorbic acid, preferably citric acid for adjusting a pH value, which serves as a stabilizing agent by using its weak acidity to prevent the ginkgolides from being subjected to loop opening under an alkaline condition. The reason is that the structure of the ginkgolides is a five-membered ring, which is stable under a weak acidity condition; and the citric acid is a weak acid, which may prevent the ginkgolides from being subjected to loop opening under an alkaline condition.

A purpose of refrigerating in the step A is to enable oil and water to separate to get rid of lipid-soluble impurities in water.

B. Extracting: firstly extracting a concentrated solution with n-hexane or petroleum ether 2 to 3 times (preferably, extracting with isometric n-hexane or petroleum ether), extracting an aqueous phase with a lipid-soluble solvent 4 to 5 times (preferably, extracting with isometric ethyl acetate), secondly extracting with water saturated sec-butyl alcohol (n-butanol)-ethyl acetate mixed solvent 4 to 5 times (preferably, extracting with isometric water saturated sec-butyl alcohol-ethyl acetate mixed solvent), combining organic phase extracted solutions, and concentrating under reduced pressure concentration.

Wherein, firstly extracting with the n-hexane or petroleum ether is to remove impurities of chlorophyll, ginkgolic acid, etc.

Secondly the ginkgolides are extracted with the lipid-soluble solvent, wherein the available lipid-soluble solvent includes at least one of ethyl acetate, ethyl formate, acetone and butanone.

Ginkgo terpene lactones are freely soluble in the ethyl acetate; the solubility of ginkgo flavonoids in the ethyl acetate is relatively low, but relative high in hot water and water-containing alcohol, thus the ginkgolides can be extracted with the ethyl acetate to be separated from ginkgo flavonoids; and the separated crude ginkgolides may be subjected to adsorption chromatography by using active carbon, silica gel or a resin column to further get rid of impurities, and then crystallized in the water-containing alcohol so that purer ginkgolides may be obtained.

C. Passing through a column: enabling the extracted solution to pass through a polyamide (30 to 60 mesh) resin column, sequentially eluting with 1 to 5 BV of water, 3 to 5 BV of 20% to 40% v/v ethanol and 2 to 3 BV of 60% to 90% v/v ethanol, controlling the flow velocity of eluants to 2 to 3 BV/h; and combining the eluants, concentrating under reduced pressure, and drying.

D. Separating crystals out: adding a dry substance after passing through the column in boiling water, dissolving by agitating, cooling, extracting a supernate with isometric ethyl acetate, ethyl formate or acetone 4 to 5 times, combining extracted solutions, concentrating under reduced pressure, drying by distillation, adding 5 to 8 times of amount of 30% to 50% v/v ethanol, dissolving by heating and agitating, filtering, refrigerating, separating crystals out, filtering to obtain a filtrate I for later use, washing the crystals with 30% to 50% v/v ethanol, drying under reduced pressure to obtain crystals I.

Concentrating the filtrate I until the alcohol content is 10% to 30% v/v, refrigerating, separating crystals out, filtering to obtain a filtrate II for later use; and washing with 30% to 50% v/v ethanol, and drying under reduced pressure to obtain crystals II.

Concentrating the filtrate II, adding 0.1 to 0.5% (g/L) active carbon for adsorption, filtering to obtain a filtrate, concentrating the filtrate until the alcohol content is 10% to 30% v/v, refrigerating, separating crystals out, filtering to obtain a filtrate III for later use, washing the crystals with 30% to 50% v/v ethanol, and drying under reduced pressure to obtain crystals III.

Concentrating the filtrate III, passing through an active carbon-silica gel (volume ratio of 1:1 to 1:3) column, firstly eluting with 30% to 50% v/v ethanol, then eluting with 70% to 90% v/v ethanol, collecting eluants, concentrating until the alcohol content is 10% to 30% v/v, refrigerating and separating crystals out, filtering the crystals out to obtain a filtrate IV for later use; and washing the crystals with 30% ethanol, and drying under reduced pressure to obtain crystals IV.

Concentrating the filtrate IV, refrigerating, separating crystals out, filtering, washing the crystals with 30% v/v ethanol, and drying under reduced pressure to obtain crystals V.

It is determined whether to crystallize the filtrate IV according to a detection result of HPLC to residual ginkgolides in a mother solution.

E. Mixing the crystals: uniformly mixing the crystals I, II, III, IV and V, crushing to obtain an off white crystal compound, wherein the HPLC content of effective parts (a sum of bilobalide, ginkgolide A, ginkgolide B and ginkgolide C) of the crystal compound is greater than 95%.

Parameters of ginkgolides, obtained by adopting the method for extracting and separating the ginkgolides according to an embodiment of the present invention are as follows:

a) Property: off white color or slightly yellowish crystalline powder. The ginkgolides are freely soluble in ethyl acetate, soluble in methanol and ethanol, and hardly soluble in water.

b) Water content: less than 5.0%.

c) Protein: absorbance of less than 0.05 at a 595 nm wavelength.

d) Tannin, resin, oxalate and potassium ion: not detected.

e) Residual solvents: contents of the ethanol and the ethyl acetate are both less than 0.5%, the content of the n-hexane is less than 0.029%, and the content of caprolactam is less than 0.0015%.

f) Total ginkgoic acid: an HPLC determines that the content of the total ginkgoic acid is less than 5 ppm.

g) Macromolecules and polymers: a gel chromatography determines that no residual macromolecules and polymers exist. AN LC to MS determines that no macromolecules and polymers with molecular weight of greater than 1000 exist.

h) Heavy metals: less than 10 ppm.

i) arsenic salt: less than 2 ppm.

k) Undue toxicity: a prepared solution containing 0.2 mg of ginkgolides each ml meets the requirement of administration of an intravenous injection method.

l) Fingerprint: an HPLC method determines that the similarity of four common peaks is greater than 0.95 according to a traditional Chinese medicine chromatographic fingerprint similarity evaluating system with a bilobalide control, a ginkgolide A control, a ginkgolide B control and a ginkgolide C control as reference substances.

m) Content: an HPLC method determines that calculated on the dry substance, the content of the bilobalide ($C_{15}H_{18}O_8$) is 25.0% to 50.0%, the content of the ginkgolide A ($C_{20}H_{24}O_9$) is 20.0% to 45.0%, the content of the ginkgolide B ($C_{20}H_{24}O_{10}$ is 10.0% to 30.0% and the content of the ginkgolide C ($C_{20}H_{24}O_{11}$) is 5.0% to 15.0%, and the total amount of the bilobalide, the ginkgolide A, the ginkgolide B and the ginkgolide C is greater than 95%.

DETAILED DESCRIPTION

Figure 1:
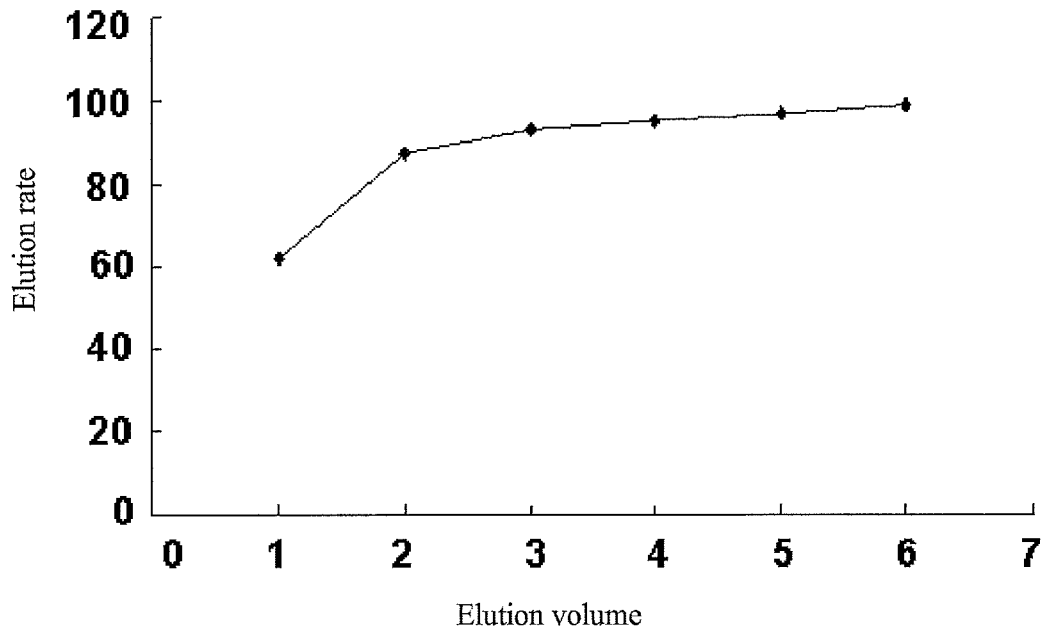
FIG. 1 shows the influence of elution volume on elution rate.

The followings are tests for screening key conditions in a method for preparing ginkgolides of the present invention.

Tests for Screening Extraction Schemes

Method I: a concentrated solution was extracted with isometric n-hexane 2 to 3 times, an aqueous phase was extracted with 8 times of butanone-acetone (4:6) under the warming condition—5 times, extracted solutions were combined, and concentrated under reduced pressure.

Method II: a concentrated solution was extracted with isometric n-hexane 2 to 3 times, and then an aqueous phase was extracted with isometric ethyl acetate 4 to 5 times, and extracted with equivalent saturated sec-butyl alcohol-ethyl acetate (7:3) 4 to 5 times, and extracted solutions were combined, concentrated under reduced pressure, and dried.

The above tests for screening two extraction, separation and purification methods respectively determined the total amounts of the ginkgolides in the two tests by using an HPLC to ELSD method, with test results seen in Table 1.

TABLE 1

Test results in screening of extraction schemes

| Project | Method I | Method II |
|---|---|---|
| Appearance | Brown powder | Brown powder |
| Content of total lactone | 14.1 | 10.8 |

The content of the total lactone, obtained in the method II, was higher, and ethyl acetate and sec-butyl alcohol were solvents with extremely high safety, and therefore, the method II was selected to be used as an extraction, separation and purification process.

II. Tests for Screening Chromatographic Conditions

Because an extracted solution still contained a plenty of ginkgo flavonoids and other impurities, the flavonoids must be effectively separated from the ginkgolides if the ginkgolides with extremely high purity were to be obtained. Separation methods commonly adopted at present comprised a polyamide resin column separation method, an aluminum oxide column chromatography and a silica gel column chromatography, and the inventor compared research processes and results as follows:

Method I: an extracted solution was enabled to pass through a polyamide resin column, firstly eluted with 2 to 3 times of amount of 30% ethanol, then eluted with 70% ethanol at an eluting speed of 2 BV/h; and eluants were concentrated and dried by distillation.

Method II: an extracted solution was enabled to pass through an acidic aluminum oxide column, mixed with equivalent aluminum oxide, dried, applied to a column by adopting a dry process, eluted with 4 to 6 times of amount of ethyl acetate at an eluting speed of 2 BV/h; and an eluant was concentrated and dried by distillation.

Method III: an extracted solution was enabled to pass through a silica gel column, mixed with equivalent column chromatography silica gel, dried, applied to a column by adopting a dry process, firstly eluted with 4 to 6 times of amount of petroleum ether to ethyl acetate (2:1) at an eluting speed of 2 BV/h, and then eluted with n-hexane-ethyl acetate (5:1) at an eluting speed of 2 BV/h; and eluants were concentrated and dried by distillation.

AN HPLC-ELSD method was used for respectively determining contents of the ginkgolides in the three tests, with test results seen in Table 2.

TABLE 2

Test results of column chromatography

| Project | Method I | Method II | Method III |
|---|---|---|---|
| Appearance | Yellow powder | Yellow powder | Yellow powder |
| Content of total lactone (%) | 47.8 | 35.5 | 38.2 |

It can be seen that from the above, the content of the ginkgolides, obtained by adopting the polyamide resin column, is higher, and the separation effect is better.

Polyamide resin has a better function of adsorbing flavonoids, therefore the ginkgolides may be effectively separated from the ginkgo flavonoids to consider parameters of processes of passing through the column and eluting.

1. Selection of washing volume: distilled water was used for washing a resin column to be capable of playing a good role of getting rid of impurities, 5 BV of water was used for washing the resin column at a flow velocity of 1 to 2 BV/h, the color of effluent is changed from deep to shallow, 5 BV of washed solution was collected, effluent was clear, detection results indicated that when the water volume reaches 3 BV, water-soluble impurities in the column had been basically cleaned, no ginkgolides were detected, and thus a washing volume of 3 BV is selected. The influence of the elution volume on the elution rate is seen in FIG. 1.

Influence of ethanol eluting concentration on eluting effect: an extractant was respectively applied to different polyamide columns, adsorbed for 30 min, firstly washed with 3 BV of water, and then eluted respectively with 10%, 30%, 40%, 50%, 70% and 90% ethanol at a flow velocity of 1 BV/h; ethanol eluants were respectively collected, contents of the ginkgolides in the eluants of all concentrations were determined; with the rise of the concentration of the ethanol, the elution amount and the elution rate were increased therewith, but the elution amount was increased slowly when the concentration of the ethanol reached 40%, there was a little difference between the elution amount when the concentration of the ethanol was 40% and the elution amount when the concentration of the ethanol was 90%, and a preferred elution rate was reached basically when the concentration of the ethanol reached 30%, and thus the 30% ethanol was adopted as a preferred eluting concentration.

Figure 2:
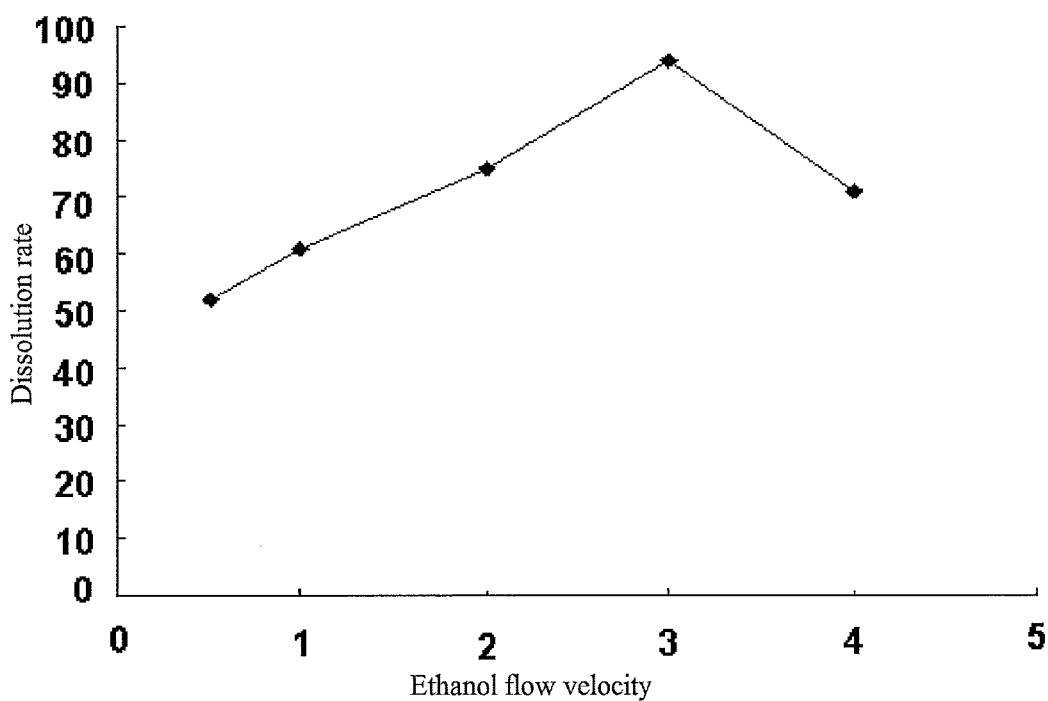
FIG. 2 shows the influence of ethanol flow velocity on elution rate.

3. Influence of ethanol dissolution flow velocity on eluting effect: an extractant was respectively applied to different polyamide columns, adsorbed for 30 min, firstly washed with 3 BV of water, and then eluted with 40% ethanol at a flow velocity of 1 BV/h. For selecting a preferred ethanol dissolution flow velocity, the extractant is enabled to pass through column respectively at flow velocities of 1, 2, 3, 4 and 5 BV/h, and eluted; an eluant was collected, and the contents of the ginkgolide were determined. There is a great relevance between the eluting flow velocity and the dissolution rate, with the rise of the flow velocity, the dissolution rate was increased, but reduced when the flow velocity reached 3 BV/h. This is because the ethanol eluant might not be well exchanged with the adsorbed ginkgolides due to speed increase to cause that good eluting effect could not be achieved. The preferred flow velocity was 2 to 3 BV/h. The influence of the ethanol flow velocity on the elution rate is seen in FIG. 2.

III: Tests for Screening Conditions of Separating Crystals Out

Although the content of the ginkgolides in the extractant obtained after passing through the column and extracting had increased, and flavonoids were effectively separated, the content of the ginkgolides had not met the requirement of an injection yet, and the ginkgolides were required being crystallized and purified. The ginkgolides were freely soluble in solvents of the ethanol, the ethyl acetate, etc., and not soluble in solvents of water, n-hexane, etc., therefore, a polarity-fitting mixed solvent was only selected to be used as a crystallization solvent.

(1) 30% v/v ethanol solvent: an extractant to be separated crystals out was measured, respectively added with 4, 6, 8 and 10 times of amount of 30% ethanol, dissolved by heating, let to stand at a low temperature (0 to 6° C.), filtered, and dried under reduced pressure; and weights of crystals were respectively determined, with test results seen in Table 3.

TABLE 3

Test results of crystallization with 30% ethanol

| | Solvent addition amount (times) | | | |
|---|---|---|---|---|
| | 4 | 6 | 8 | 10 |
| Status of heating solvent | Un-dissolved completely | Dissolved completely | Dissolved completely | Dissolved completely |
| Crystal amount (g) | 3.8 | 4.5 | 4.2 | 2.4 |

During separating crystals out, adding 5 to 8 times of amount of 30% ethanol would be more appropriate.

(2) n-hexane-ethyl acetate (8:1) solvent: 10 g of extractant to be separated crystals out was measured, respectively added with 4, 6, 8 and 10 times of amount of n-hexane-ethyl acetate (8:1) mixed solvent, dissolved by heating, let to stand at a low temperature (0 to 6° C.), filtered, and dried under reduced pressure; and weights of crystals were respectively determined, with test results seen in Table 4.

Table 4 Test results of crystallization with n-hexane-ethyl acetate mixed solvent

TABLE 4

Test results of crystallization with normal hexane-ethyl acetate mixed solvent

| | Solvent addition amount (times) | | | |
|---|---|---|---|---|
| | 4 | 6 | 8 | 10 |
| Status of heating solvent | Dissolved completely | Dissolved completely | Dissolved completely | Dissolved completely |
| Crystal amount (g) | 2.3 | 3.5 | 3.8 | 3.2 |

The amount of separating the crystals out by the n-hexane-ethyl acetate mixed solvent was less than that of the 30% ethanol solvent.

(3) 10% v/v ethyl acetate solvent: 10 g of extractant to be separated crystals out was measured, respectively added with 4, 6, 8 and 10 times of amount of 10% ethyl acetate, dissolved by heating, let to stand at a low temperature (0 to 6° C.), filtered, and dried under reduced pressure; and weights of crystals were respectively determined, with test results seen in Table 5.

TABLE 5

Test results of crystallization with 10% v/v ethyl acetate

| | Solvent addition amount (times) | | | |
|---|---|---|---|---|
| | 4 | 6 | 8 | 10 |
| Status of heating solvent | Un-dissolved completely | Dissolved completely | Dissolved completely | Dissolved completely |
| Crystal amount (g) | 2.3 | 3.5 | 3.3 | 2.2 |

The amount of separating the crystals out by the 10% v/v ethyl acetate solvent was less than that of the 30% ethanol solvent.

According to an experimental result, selecting 5 to 8 times of amount of 30% ethanol as the crystallization solvent was more appropriate.

The followings are examples of preparing ginkgolides by adopting a method of the present invention.

Example 1

To 50 kg of coarse ginkgo leaf powder, 65% ethanol is added. The mixture obtained from the above is extracted 3 times (10, 8 and 6 times of amount of 65% ethanol) by heating with an inverse flow, 1.5 h a time. Extracted solutions are combined, filtered, concentrated under reduced pressure, and dissolved by adding 0.05% methionine. The pH value is adjusted to 4 to 5 with a citric acid solution. The extracted solutions treated as above are continuously concentrated, let to stand at a low temperature, and filtered. The extracted solutions treated as above are extracted with equivalent ethyl acetate, finally extracted with a water saturated sec butyl alcohol ethyl acetate mixed solvent, enabled to pass through a polyamide (30 to 60 mesh) resin column, eluted with water firstly, then eluted with 30% ethanol, and then eluted with 70% ethanol. Eluants are combined, and concentrated under reduced pressure. The eluants treated as above are added in 2 to 3 times of amount of boiling water, dissolved by agitating, let to stand, cooled, extracted with ethyl acetate, concentrated under reduced pressure, dissolved by adding ethanol through heating and agitating, filtered, and cooled to separate crystals out; and the crystals are filtered, and dried to obtain crystals I (mainly including bilobalide and ginkgolide B). The filtrate treated as above is continuously concentrated, added with ethanol until the concentration reaches 30%, and let to stand to separate crystals out; and the crystals are filtered, and dried to obtain crystals II (mainly including ginkgolides A, B and C). The filtrate treated as above is added with medicinal charcoal, adsorbed by agitating, filtered, concentrated and cooled to separate crystals out; and the crystals are filtered, and dried to obtain crystals III (mainly including ginkgolides A and B). The filtrate treated as above is concentrated, enabled to pass through a medicinal charcoal-silica gel (1:1) column, firstly eluted with 2 times of amount of 30% ethanol, and then eluted with 4 times of amount of 70% ethanol; eluants are collected, concentrated, added with the ethanol until the concentration reaches 30%, cooled, let to stand to separate crystals out; and the crystals are filtered, and dried to obtain crystals IV. The filtrate treated as above is concentrated, added with the ethanol until the concentration reaches 30%, cooled, and let to stand to separate crystals out; and the crystals are filtered, and dried to obtain crystals V. The crystals are uniformly mixed to obtain 91.6 g of ginkgolides, with HPLC content of 97.2%, wherein the content of bilobalide ($C_{15}H_{18}O_8$) is 42.5%, the content of the ginkgolide A ($C_{20}H_{24}O_9$) is 25.4%, the content of the ginkgolide B ($C_{20}H_{24}O_{10}$) is 18.7%, and the content of the ginkgolide C ($C_{20}H_{24}O_{11}$) is 10.6%.

Example 2

To 200 kg of coarse ginkgo leaf powder, 6 times of amount of 80% ethanol is added. The mixture obtained from the above is extracted 3 times by heating with an inverse flow, 1.5 h a time. Extracted solutions are combined, and filtered. A filtrate is exposed to reduced pressure to recover the ethanol until no alcohol taste exists, and dissolved by adding 0.05% methionine by agitating. The pH value is adjusted to 4 to 5 with a citric acid solution. The filtrate treated as above is continuously concentrated, let to stand at a low temperature, and filtered. The filtrate treated as above is extracted with n-hexane, then with ethyl acetate, finally extracted with a water saturated sec-butyl alcohol-ethyl acetate mixed solvent, enabled to pass through a polyamide (30 to 60 mesh) resin column, eluted with 30% ethanol firstly, and then eluted with 70% ethanol. Eluants are combined, and concentrated under reduced pressure. The eluants treated as above are added in boiling water, dissolved by agitating, let to stand, cooled, extracted with ethyl acetate, concentrated under reduced pressure, dissolved by adding ethanol by heating and agitating, filtered, and cooled to separate crystals out; and the crystals are filtered, and dried to obtain crystals I (mainly including bilobalide and ginkgolide B). The filtrate treated as above is continuously concentrated, added with ethanol, and let to stand to separate crystals out; and the crystals are filtered, and dried to obtain crystals II (mainly including ginkgolides A, B and C). The filtrate treated as above is added with medicinal charcoal, adsorbed by agitating, filtered, concentrated, added with the ethanol, and cooled to separate crystals out; and the crystals are filtered, and dried to obtain crystals III (mainly including ginkgolides A and B). The filtrate treated as above is concentrated, enabled to pass through a medicinal charcoal-silica gel (1:1) column, firstly eluted with 2 times of amount of 30% ethanol, and then eluted with 4 times of amount of 70% ethanol; eluants are collected, concentrated, added with the ethanol until the concentration reaches 30%, cooled, let to stand to separate crystals out; and the crystals are filtered, and dried to obtain crystals IV. The filtrate is concentrated, added with the ethanol until the concentration reaches 30%, cooled, and let to stand to separate crystals out; and the crystals are filtered, and dried to obtain crystals V. The crystals are uniformly mixed to obtain 362.8 g of ginkgolides, with HPLC content of 96.8%, wherein the content of bilobalide ($C_{15}H_{18}O_8$) is 31.2%, the content of the ginkgolide A ($C_{20}H_{24}O_9$) is 28.8%, the content of the ginkgolide B ($C_{20}H_{24}O_{10}$) is 28.2%, and the content of the ginkgolide C ($C_{20}H_{24}O_{11}$) is 8.6%.

Example 3

To 200 kg of coarse ginkgo leaf powder, 8 times of amount of 80% ethanol is added. The mixture obtained from the above is extracted 3 times by heating with an inverse flow, 1.5 h a time. Extracted solutions are combined, and filtered. A filtrate is exposed to reduced pressure to recover the ethanol until no alcohol taste exists, and dissolved by adding 0.05% methionine by agitating. The pH value is adjusted to 4 to 5 with a citric acid solution. The filtrate treated as above is continuously concentrated, let to stand at a low temperature, and filtered. The filtrate treated as above is extracted with n-hexane, then with ethyl acetate, finally extracted with a water saturated sec-butyl alcohol-ethyl acetate mixed solvent, enabled to pass through a polyamide (30 to 60 mesh) resin column, eluted with 30% ethanol firstly, and then eluted with 75% ethanol. Eluants are combined, and concentrated under reduced pressure. The eluants treated as above are added in boiling water, dissolved by agitating, let to stand, cooled, extracted with ethyl acetate, concentrated under reduced pressure, dissolved by adding ethanol through heating and agitating, filtered, and cooled to separate crystals out; and the crystals are filtered, and dried to obtain crystals I (mainly including bilobalide and ginkgolide B). The filtrate treated as above is continuously concentrated, added with ethanol, and let to stand to separate crystals out; and the crystals are filtered, and dried to obtain crystals II (mainly including ginkgolides A, B and C). The filtrate treated as above is added with medicinal charcoal, adsorbed by agitating, filtered, concentrated, added with the ethanol, and cooled to separate crystals out; and the crystals are filtered, and dried to obtain crystals III (mainly including ginkgolides A and B). The filtrate treated as above is concentrated, applied to a medicinal charcoal-silica gel (1:1) column, and eluted with 60% ethanol; an eluant is collected, concentrated, and cooled to separate crystals out; and the crystals are filtered, and dried to obtain crystals IV. The crystals are uniformly mixed to obtain 375.5 g of ginkgolides, with HPLC content of 97.1%, wherein the content of bilobalide ($C_{15}H_{18}O_8$) is 35.8%, the content of the ginkgolide A ($C_{20}H_{24}O_9$) is 28.5%, the content of the ginkgolide B ($C_{20}H_{24}O_{10}$) is 26.2%, and the content of the ginkgolide C ($C_{20}H_{24}O_{11}$) is 6.6%.

Example 4

To 200 kg of coarse ginkgo leaf powder, 10 times of amount of 75% ethanol is added. The mixture obtained from the above is extracted 3 times by heating with an inverse flow, 1.5 h a time. Extracted solutions are combined, and filtered. A filtrate is exposed to reduced pressure to recover the ethanol until no alcohol taste exists, and dissolved by adding 0.05% methionine by agitating. The pH value is adjusted to 4 to 5 with a citric acid solution. The filtrate treated as above is continuously concentrated, let to stand at a low temperature, and filtered. The filtrate treated as above is extracted with n-hexane, then with ethyl acetate, finally extracted with a water saturated sec-butyl alcohol-ethyl acetate mixed solvent, enabled to pass through a polyamide (30 to 60 mesh) resin column, eluted with 25% ethanol firstly, and then eluted with 65% ethanol. Eluants are combined, and concentrated under reduced pressure. The eluants treated as above are added in boiling water, dissolved by agitating, let to stand, cooled, extracted with ethyl acetate, concentrated under reduced pressure, dissolved by adding 50% ethanol through heating and agitating, filtered, and cooled to separate crystals out; and the crystals are filtered, and dried to obtain crystals I (mainly including bilobalide and ginkgolide B). The filtrate treated as above is continuously concentrated, added with ethanol, and let to stand to separate crystals out; and the crystals are filtered, and dried to obtain crystals II (mainly including ginkgolides A, B and C). The filtrate treated as above is added with medicinal charcoal, adsorbed by agitating, filtered, concentrated, added with the ethanol, and cooled to separate crystals out; and the crystals are filtered, and dried to obtain crystals III (mainly including ginkgolides A and B). The filtrate treated as above is concentrated, applied to a medicinal charcoal-silica gel (1:1) column, and eluted with 60% ethanol; an eluant is collected, concentrated, cooled, let to stand to separate crystals out; and the crystals are filtered, and dried to obtain crystals IV. The filtrate treated as above is concentrated, cooled, and let to stand to separate crystals out;

and the crystals are filtered, and dried to obtain crystals V. The crystals are uniformly mixed to obtain 362.2 g of ginkgolides, with HPLC content of 96.5%, wherein the content of bilobalide ($C_{15}H_{18}O_8$) is 35.5%, the content of the ginkgolide A ($C_{20}H_{24}O_9$) is 26.0%, the content of the ginkgolide B ($C_{20}H_{24}O_{10}$) is 26.2%, and the content of the ginkgolide C ($C_{20}H_{24}O_{11}$) is 8.8%.

Example 5

To 200 kg of coarse ginkgo leaf powder, 8 times of amount of 60% ethanol is added. The mixture obtained from the above is extracted 3 times by heating with an inverse flow, 1.5 h a time. Extracted solutions are combined, and filtered. A filtrate is exposed to reduced pressure to recover the ethyl acetate, and dissolved by adding 0.05% methionine by agitating. The pH value is adjusted to 4 to 5 with a citric acid solution. The filtrate treated as above is continuously concentrated, let to stand at a low temperature, and filtered. The filtrate treated as above is extracted with petroleum ether firstly, and then an aqueous phase is extracted with ethyl acetate, finally extracted with a water saturated sec-butyl alcohol-ethyl acetate mixed solvent, enabled to pass through a polyamide (30 to 60 mesh) resin column, eluted with 30% ethanol firstly, and then eluted with 75% ethanol. Eluants are combined, and concentrated under reduced pressure. The eluants treated as above are added in boiling water, dissolved by agitating, let to stand, cooled, extracted with acetone, concentrated under reduced pressure to dry, dissolved by adding 50% ethanol through heating and agitating, filtered, and cooled to separate crystals out; and the crystals are filtered, and dried to obtain crystals I (mainly including bilobalide and ginkgolide B). The filtrate treated as above is continuously concentrated, added with ethanol, and let to stand to separate crystals out; and the crystals are filtered, and dried to obtain crystals II (mainly including ginkgolides A, B and C). The filtrate treated as above is added with medicinal charcoal, adsorbed by agitating, filtered, concentrated, added with the ethanol, and cooled to separate crystals out; and the crystals are filtered, and dried to obtain crystals III (mainly including ginkgolides A and B). The filtrate treated as above is concentrated, applied to a medicinal charcoal-silica gel (1:1) column, and eluted with 60% ethanol; an eluant is collected, concentrated, cooled, let to stand to separate crystals out; and the crystals are filtered, and dried to obtain crystals IV. The crystals are uniformly mixed to obtain 350.6 g of ginkgolides, with HPLC content of 97.4%, wherein the content of bilobalide ($C_{15}H_{18}O_8$) is 40.0%, the content of the ginkgolide A ($C_{20}H_{24}O_9$) is 22.5%, the content of the ginkgolide B ($C_{20}H_{24}O_{10}$) is 27.2%, and the content of the ginkgolide C ($C_{20}H_{24}O_{11}$) is 10.3%.

Example 6

To 200 kg of coarse ginkgo leaf powder, 8 times of amount of 50% ethanol is added. The mixture obtained from the above is extracted 3 times by heating with an inverse flow, 1.5 h a time. Extracted solutions are combined, and filtered. A filtrate is exposed to reduced pressure to recover acetone, and dissolved by adding 0.05% methionine by agitating. The pH value is adjusted to 4 to 5 with a citric acid solution. The filtrate treated as above is continuously concentrated, let to stand at a low temperature, and filtered. The filtrate treated as above is extracted with petroleum ether firstly, and then an aqueous phase is extracted with ethyl acetate, finally extracted with a water saturated sec-butyl alcohol-ethyl acetate mixed solvent, enabled to pass through a polyamide (30 to 60 mesh) resin column, eluted with 30% ethanol firstly, and then eluted with 70% ethanol. Eluants are combined, and concentrated under reduced pressure. The eluants treated as above are added in boiling water, dissolved by agitating, let to stand, cooled, extracted with ethyl acetate, concentrated under reduced pressure to dry, dissolved by adding 30% ethanol through heating and agitating, filtered, and cooled to separate crystals out; and the crystals are filtered, and dried to obtain crystals I (mainly including bilobalide and ginkgolide B). The filtrate treated as above is continuously concentrated, added with ethanol, and let to stand to separate crystals out; and the crystals are filtered, and dried to obtain crystals II (mainly including ginkgolides A, B and C). The filtrate treated as above is added with medicinal charcoal, agitated and adsorbed, filtered, concentrated, added with the ethanol, and cooled to separate crystals out; and the crystals are filtered, and dried to obtain crystals III (mainly including ginkgolides A and B). The filtrate treated as above is concentrated, applied to a medicinal charcoal-silica gel (1:1) column, and eluted with 60% ethanol; an eluant is collected, concentrated, and cooled to separate crystals out; and the crystals are filtered, and dried to obtain crystals IV. The filtrate treated as above is concentrated, and cooled to separate crystals out; and the crystals are filtered, and dried to obtain crystals V. The crystals are uniformly mixed to obtain 343.5 g of ginkgolides, with HPLC content of 96.2%, wherein the content of bilobalide ($C_{15}H_{18}O_8$) is 38.2%, the content of the ginkgolide A ($C_{20}H_{24}O_9$) is 28.3%, the content of the ginkgolide B ($C_{20}H_{24}O_{10}$) is 24.2%, and the content of the ginkgolide C ($C_{20}H_{24}O_{11}$) is 9.3%.

Example 7

To 200 kg of coarse ginkgo leaf powder, 8 times of amount of 70% ethanol is added. The mixture obtained from the above is decocted and extracted 3 times by heating to microboiling with an inverse flow, 1.5 h a time. Extracted solutions are combined, and filtered. A filtrate is exposed to reduced pressure to recover ethanol, and dissolved by adding 0.05% methionine by agitating. The pH value is adjusted to 4 to 5 with a citric acid solution. The filtrate treated as above is continuously concentrated, let to stand at a low temperature, and filtered. The filtrate treated as above is extracted with petroleum ether firstly, and then an aqueous phase is extracted with ethyl acetate, finally extracted with a water saturated sec-butyl alcohol-ethyl acetate mixed solvent, enabled to pass through a polyamide (30 to 60 mesh) resin column, eluted with 30% ethanol firstly, and then eluted with 70% ethanol. Eluants are combined, and concentrated under reduced pressure. The eluants treated as above are added in boiling water, dissolved by agitating, let to stand, cooled, extracted with ethyl acetate, concentrated under reduced pressure to dry, dissolved by adding 30% ethanol through heating and agitating, filtered, and cooled to separate crystals out; and the crystals are filtered, and dried to obtain crystals I (mainly including bilobalide and ginkgolide B). The filtrate treated as above is continuously concentrated, added with ethanol, and let to stand to separate crystals out; and the crystals are filtered, and dried to obtain crystals II (mainly including ginkgolides A, B and C). The filtrate treated as above is added with medicinal charcoal, adsorbed by agitating, filtered, concentrated, added with the ethanol, and cooled to separate crystals out; and the crystals are filtered, and dried to obtain crystals III (mainly including ginkgolides A and B). The filtrate treated as above is concentrated, applied to a medicinal charcoal-silica gel (1:1) column, and eluted with 60% ethanol; an eluant is collected, concentrated, and cooled to separate crystals out; and the crystals are filtered, and dried to obtain crystals IV. The filtrate treated as above is concentrated, and cooled to separate crystals out; and the crystals are filtered, and dried to obtain crystals V. The crystals are uniformly mixed to obtain 362.6 g of ginkgolides, with HPLC content of 97.4%, wherein the content of bilobalide ($C_{15}H_{18}O_8$) is 36.5%, the content of the ginkgolide A ($C_{20}H_{24}O_9$) is 25.3%, the content of the ginkgolide B ($C_{20}H_{24}O_{10}$) is 28.2%, and the content of the ginkgolide C ($C_{20}H_{24}O_{11}$) is 7.4%.

To sum up, ginkgolides with higher purity and relatively fixed components may be obtained by adopting the extraction, separation and purification method used by the present invention, wherein the content of bilobalide ($C_{15}H_{18}O_8$) is 25.0% to 50.0%, the content of the ginkgolide A ($C_{20}H_{24}O_9$) is 20.0% to 45.0%, the content of the ginkgolide B ($C_{20}H_{24}O_{10}$ is 10.0% to 30.0%, and the content of the ginkgolide C ($C_{20}H_{24}O_{11}$) is 5.0% to 15.0%, and the total amount of the bilobalide, the ginkgolide A, the ginkgolide B and the ginkgolide C is greater than 95%.

Subentry detection methods of ginkgolides and detection results of the present invention are as follows:

a) Property: off white color or slightly yellowish crystalline powder.

The ginkgolides are freely soluble in ethyl acetate, soluble in methanol and ethanol, and hardly soluble in water.

b) Water content: drying under reduced pressure at a temperature of 60° C. until the mass loss is reduced to less than 5.0%.

c) Protein: absorbance of less than 0.05 at a 595 nm wavelength.

Measuring about 24 mg of ginkgolides of the present invention, and dissolving by adding 2 ml of ethanol, and diluting to 50 ml by adding water as a test solution. A Coomassie brilliant blue method (Bradford method) determines that the absorbance at a 595 nm wavelength is less than 0.05 by using a corresponding reagent as a blank.

d) Tannin, resin, oxalate and potassium ion: not detected.
Available Detection Methods Include:

Tannin: measuring 1 ml of protein inspection item test solution, adding 1 drop of dilute acetic acid, then adding 5 drops of gelatin sodium chloride test solution, shaking well, and placing for 10 min, without turbidity or precipitation.

Resin: measuring 5 ml of protein inspection item test solution, adding 1 drop of hydrochloric acid, and placing for 30 min, without separating resinoids out.

Oxalate: measuring 2 ml of protein inspection item test solution, adjusting the pH value to 1 to 2 with diluted hydrochloric acid, filtering, adjusting the pH value of a filtrate to 5 to 6 with ammonia water, adding 3 drops of 3% calcium chloride solution, and placing for 10 min, without turbidity or precipitation.

Potassium ion: measuring 2 ml of protein inspection item test solution, placing in a 10 ml Nessler tube, adding 0.6 ml of alkaline formaldehyde solution, 2 drops of 3% EDTA solution and 0.5 ml of 3% sodium tetraphenylborate solution, diluting to 10 ml by adding water; and in addition, measuring 0.8 ml of standard potassium chloride solution, and testing by using the same method, wherein the turbidity of the test solution is not greater that of a reference solution.

Result: tannin, resin, oxalate and potassium ion are not detected.

e) Residual solvents:
(1) Ethanol, ethyl acetate and n-hexane: contents of the ethanol and the ethyl acetate are both less than 0.5%, and the content of the n-hexane is less than 0.029%.

(2) Resin residual amount: the content of caprolactam is less than 0.0015%.

f) Total ginkgoic acid: the content of the total ginkgoic acid is less than 5 ppm.

g) Macromolecules and polymers: a gel chromatography determines that no residual macromolecules and polymers exist. AN LC-MS determines that no macromolecules and polymers with molecular weight of greater than 1000 exist.

Determination Methods:

(1) Gel chromatography: chromatographic column: Phenomenex BioSep-SEC-S2000, 300×7.8 mm, Sum; mobile phase: 0.71% (containing 0.02% of sodium azide) sodium sulfate solution; column temperature: 35° C.; detector temperature: 35° C.; and flow velocity: 0.5 ml/min. Result: no residual macromolecules and polymers.

(2) HPLC-MS: mobile phase: methanol-water (90:10); chromatographic column: Agilent RX-$C_{18}$ (2.1×50 mm); column temperature: 25° C.; and flow velocity: 0.3 ml/min. Result: no macromolecules and polymers with molecular weight of greater than 1000.

h) Heavy metals: less than 10 ppm.
i) arsenic salt: less than 2 ppm.

k) Undue toxicity: a prepared solution containing 0.2 mg of ginkgolides each 1 ml meets the requirement of administration of an intravenous injection method.

Preparation of a test solution: measuring about 25 mg of ginkgolides of the present invention, adding a sodium chloride injection after dissolving with 2 ml of ethanol to prepare a solution containing 0.2 mg of ginkgolides each 1 ml.

Inspection method: taking 5 mice with weight of 17 to 20 g, and injecting 0.5 ml of test solution in caudal veins of the mice, without death within 48 h.

i) Fingerprint: an HPLC method determines that a 60 min chromatogram map is recorded. The similarity of four common peaks is greater than 0.95 according to a traditional Chinese medicine chromatographic fingerprint spectrum similarity evaluating system.

m) Content: an HPLC method determines that calculated on the dry substance, the content of the bilobalide ($C_{15}H_{18}O_8$) should be 25.0% to 50.0%, the content of the ginkgolide A ($C_{20}H_{24}O_9$) should be 20.0% to 45.0%, the content of the ginkgolide B ($C_{20}H_{24}O_{10}$) should be 10.0% to 30.0% and the content of the ginkgolide C ($C_{20}H_{24}O_{11}$) should be 5.0% to 15.0%, and the total amount of the bilobalide, the ginkgolide A, the ginkgolide B and the ginkgolide C is greater than 95%.

Detection methods adopted in l) fingerprint and m) content determination are same, and conditions are as follows: filling agent: octadecyl silane bonded silica gel; mobile phase: methanol-tetrahydrofuran-water (25:10:65); evaporative light-scattering detector, drift tube temperature: 105° C.; carrier gas flow velocity: 3.00 L/min; column temperature: 40° C.; and the number of theoretical plates should be not less than 2500 calculated on a bilobalide peak. The separation degree of the bilobalide peak and a ginkgolide C peak should be greater than 1.5.

n) Pyrogen inspection: body temperature rise is lower than 0.6° C.

Preparation of a test solution: precisely weighing 20 mg of ginkgolides of the present invention, adding 2 ml of ethanol to dissolve the ginkgolides, and then adding 100 ml of 0.9% sodium chloride injection.

Inspection method: taking 3 rabbits, after determining normal body temperatures of the rabbits, within 15 min, slowly injecting the test solution in veins of ears according to an amount of 5 ml/kg each rabbit, determining body temperature once every other 30 min, 6 times in total, wherein the body temperature rise should be lower than 0.6° C., and the sum of the body temperature rises of the 3 rabbits is lower than 1.3° C.

To the above content of the present invention, the inventor determined, researched and described macromolecules and polymers for proving the technical effect of the present invention. The following test is used for further illuminating and explaining the present invention, but not limiting the present invention.

(1) Test Instruments and Reagents

An Agilent 1200 type high performance liquid chromatograph, an ultraviolet detector and a differential refraction detector.

A Phenomenex BioSep-SEC-S2000 gel chromatographic column.

A dextran control D2000 (blue dextran 2000), in the National Institute For The Control of Pharmaceutical and Biological Products, with a batch number of 140646-2000-01.

A glucose control (D0), with a content of 99.5% and a batch number of 086K0166, SIGMA.

Ultrapure water, prepared by using a Millipore-Q ultrapure water system. The rest of reagents are analytically pure.

(2) Selection of a Mobile Phone

Selecting a 0.71% (containing 0.02% of sodium azide) sodium sulfate solution as a mobile phase.

(3) Selection of a Detector

Selecting a differential refraction detector as a common detector, and this detector has better response for materials with refraction coefficient difference.

(4) Chromatographic Conditions to be Determined chromatographic column: Phenomenex BioSep-SEC-S2000, 300×7.8 mm, 5 μm Mobile phase: 0.71% (containing 0.02% of sodium azide) sodium sulfate solution Column temperature: 35° C., detector temperature: 35° C., and flow velocity: 0.5 ml/min (5) Molecular Weights of all Ingredients of Ginkgolides

|  | Ginkgolide | | | | |
|---|---|---|---|---|---|
|  | Ginkgolide A | Ginkgolide B | Ginkgolide C | Bilobalide | Ginkgolide J |
| Molecular formula | $C_{20}H_{24}O_9$ | $C_{20}H_{24}O_{10}$ | $C_{24}H_{24}O_{11}$ | $C_{15}H_{18}O_8$ | $C_{20}H_{24}O_{10}$ |
| Molecular weight | 408.4 | 424.4 | 440.4 | 326.3 | 424.4 |

(6) Methodological Study

Respectively adding a mobile phase in a dextran control and a glucose control to prepare 10 mg/ml solutions, respectively precisely drawing 20 μl of reference solutions, injecting in a chromatographic instrument, and recording chromatogram maps, results: dextran peaks at a retention time 9.816' and glucose peaks at a retention time 18.712', which indicate that a substance with large molecular weight firstly peaks and a substance with small molecular weight then peaks when a gel chromatography is adopted.

Measuring about 10 mg of ginkgolides, dissolving by adding 2 ml of alcohol, adding 1 ml of dextran reference solution (10 mg/ml), uniformly mixing, precisely drawing 10 μl injecting in a chromatographic instrument, and recording chromatogram map, results: dextran is detected at a retention time 9.698' and ingredients of a ginkgolides injection all peak after 18 min, which indicate that the peaking time is about 18 min when the molecular weight is 180 to 450 and the peaking time is about 9 min when the molecular weight is 5000 to 2000000, thus adopting a gel chromatography to detect macromolecular substances is feasible.

In order to verifying that this product does not contain macromolecules and polymers again, an LC-MS test is performed.

Chromatographic conditions: mobile phase methanol-water (90:10), chromatographic column Agilent RX-$C_{18}$ (2.1× 50 mm), column temperature 25° C., flow velocity 0.3 ml/min.

Preparation of a test solution: precisely weighing 10 mg of ginkgolides of the present invention, placing in a 10 ml measuring flask, adding a defined amount of 1% acetic acid to dissolve the ginkgolides, diluting to a scale by adding a mobile phase, and shaking well as a test solution.

LC-MS testing: according to a determined testing method, respectively weighing 10 θl of the test solution, respectively testing within ranges of molecular weights of 400 to 1000 and 400 to 3000, and recording chromatogram maps. Test results are seen in Table 6.

TABLE 6

| Test results of molecular weights in LC-MS | |
|---|---|
| $[M + Na]^+$ | M |
| 419.1, 431.5, 447.4, 463.3, 475.7, 532.2, 588.8, 701.8 | 396.1, 408.5, 424.4, 440.3, 452.7, 509.2, 678.8 |

Figure 3:
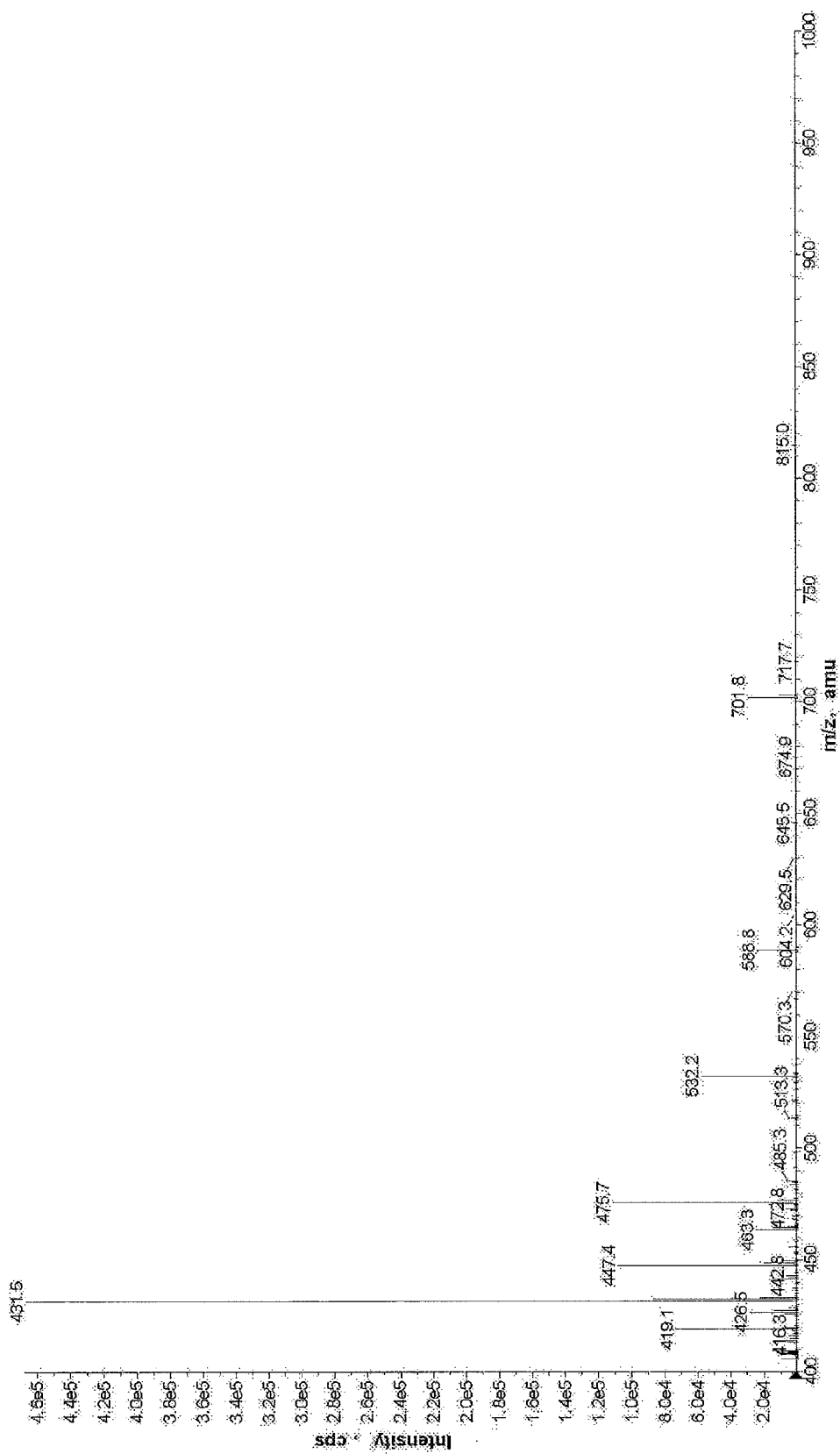
FIG. 3 is an LC-MS atlas of ginkgolides (molecular weight of 400 to 1000).
Figure 4:
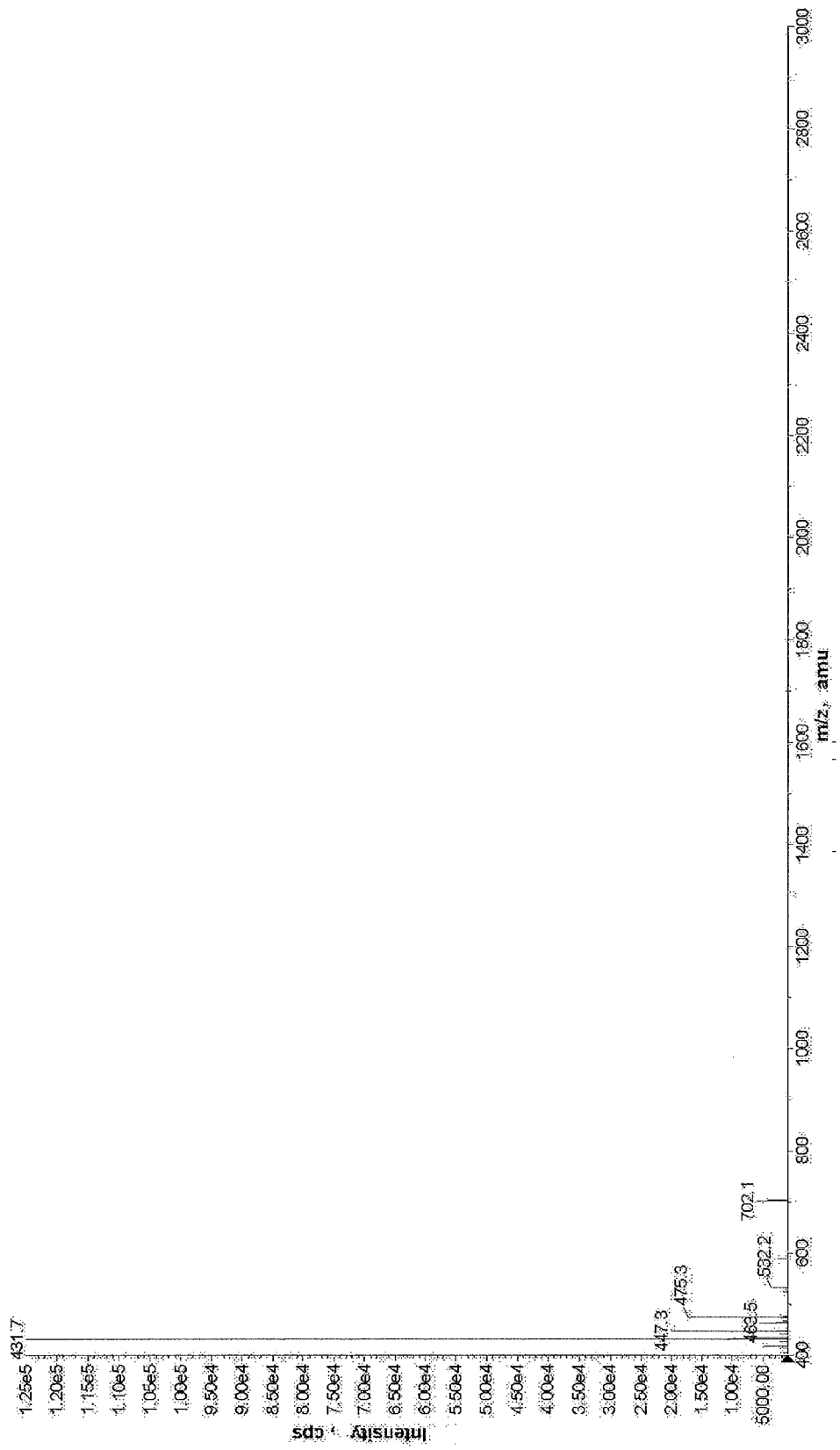
FIG. 4 is an LC-MS atlas of ginkgolides (molecular weight of 400 to 3000).

From a point of the test results of molecular weights in LC-MS of view, respectively detected ginkgolide A (molecular weight 408.5), ginkgolide B (molecular weight 424.4) and ginkgolide C (molecular weight 440.4) are completely consistent with effective ingredients of the ginkgolides of the present invention. Because the tested molecular weight ranges from 400 to 3000 and bilobalide is not tested, no sustenance with molecular weight of greater than above 700 is detected in the ginkgolides of the present invention, and other substances with different molecular weights may be other impurities. Testing molecular weights of different ingredients in the ginkgolides by the LC-MS illuminates that this product does not contain macromolecules or polymers. An LC-MS atlas of the ginkgolides is seen in FIG. 3 and FIG. 4.

Example 8

Quality control on ginkgolides-inspection of total ginkgoic acid

Chromatographic condition and system suitability test: filling agent octadecyl silane bonded silica gel; mobile phase methanol-1% glacial acetic acid (90:10); flow velocity 1.0 ml/min; and detection wavelength 310 nm. A number of theoretical plates should not be less than 4000 calculated on a ginkgoneolic acid peak.

Preparation of a reference solution: measuring a defined amount of ginkgoneolic acid control, precisely weighing, adding methanol to prepare a solution containing 5 μg of ginkgoneolic acid control each 1 ml as a reference solution; and moreover, measuring a defined amount of total ginkgoic acid control, precisely weighing, and adding methanol to prepare a solution containing 100 μg of total ginkgoic acid control each 1 ml as a location reference solution.

Preparation of a test solution: measuring 5 g of ginkgolides of the present invention, precisely weighing, placing in a flask, adding 50 ml of n-hexane, refluxing for 2 h by heating, taking out, cooling, filtering, washing a residue with a little n-hexane, combining a filtrate and a washing solution, drying by distillation on a water bath, dissolving a residue by adding methanol and diluting to 2 ml, and shaking well as a test solution.

Determination method: precisely drawing respectively 20 μl of test solution, reference solution and location reference solution, injecting in a liquid chromatograph, calculating the total peak area of a chromatographic peak corresponding to a total ginkgoic acid control in the test solution, and calculating the content of the total ginkgoic acid by using a ginkgoneolic acid control external standard method, wherein the content of the total ginkgoic acid is less than 5 ppm.

The inventor researched and illuminated the above content of the present invention for proving the technical effect of the present invention. The following test is used for further illuminating and explaining the present invention, but not limiting the present invention.

a. Method I

Preparation of a test solution: measuring 5 g of ginkgolides of the present invention, precisely weighing, placing in a flask, precisely adding 50 ml of petroleum ether (60 to 90° C.), refluxing for 2 h, taking out, cooling, filtering, washing a residue with a little petroleum ether once, combining a filtrate and a washing solution, drying by distillation on a water bath, dissolving a residue by adding methanol and diluting to 2 ml, and shaking well as a test solution (1).

Preparation of a blank sample solution: measuring 50 ml of petroleum ether (60 to 90° C.), placing in a conical flask, refluxing for 2 h, drying by distillation on a water bath, dissolving a residue by adding methanol and diluting to 2 ml, and shaking well as a blank solution (1).

b. Method II (n-Hexane Instead of Petroleum Ether)

Preparation of a test solution: measuring 5 g of ginkgolides of the present invention, precisely weighing, placing in a flask, adding 50 ml of n-hexane, refluxing for 2 h, taking out, cooling, filtering, washing a residue with a little n-hexane once, combining a filtrate and a washing solution, drying by distillation on a water bath, dissolving a residue by adding methanol and diluting to 2 ml, and shaking well as a test solution (2).

Preparation of a blank sample solution: measuring 50 ml of n-hexane, placing in a conical flask, refluxing for 2 h, drying by distillation on a water bath, dissolving a residue by adding methanol and diluting to 2 ml, and shaking well as a blank solution (2).

Determination method: precisely drawing respectively 20 μl of test solution and blank solution, injecting in a liquid chromatograph, and recording chromatogram maps.

Test results are seen in Table 7.

TABLE 7

Table for detection results of two methods

| Method | Sample | Retention time (min)/A |
| --- | --- | --- |
| Method I (petroleum ether) | Blank solution (1) | 22.207'/12408 |
|  | Test solution (1) | 22.315'/12701 |
| Method II (normal hexane) | Blank solution (2) | A chromatographic peak is not detected |
|  | Test solution (2) | A chromatographic peak is not detected |

Test results indicate that when a sample is prepared by adopting the method I (petroleum ether), a chromatographic peak is detected in the blank solution, and its peak area is basically consistent with that of the chromatographic peak detected in the test solution, which illuminate that there is interference in a blank test; and when the sample is prepared by adopting the method II (n-hexane), no chromatographic peaks are detected in the blank solution and the test solution, thus the inventor planned to adopt the method II to make a sample injection recovering test so as to verify the feasibility of the method II.

c. Sample Injection Recovering Test of Total Ginkgolic Acid

Preparation of a test solution: measuring 5 g of ginkgolides of the present invention, precisely weighing, placing in a flask, precisely adding 0.2 ml of total ginkgolic acid reference solution with a concentration of 1.032 mg/ml, precisely adding 50 ml of n-hexane, refluxing for 2 h, cooling, filtering, washing a residue with a little n-hexane, combining a filtrate and a washing solution, drying by distillation on a water bath, dissolving a residue by adding methanol and diluting to 2 ml, and shaking well as a test solution.

Preparation of a reference solution: precisely measuring 0.2 ml of total ginkgolic acid reference solution with a concentration of 1.032 mg/ml, placing in a 2 ml measuring flask, diluting to a scale by adding methanol, and shaking well as a reference solution.

Determination method: precisely drawing respectively 20 μl of test solution and reference solution, injecting in a liquid chromatograph, and recording chromatogram maps.

Results: a total ginkgoic acid chromatographic peak may be detected in the test solution on a position corresponding to a chromatography of a total ginkgoic acid control; and from a peak area point of view, peak areas of the test solution and the reference solution are consistent, which illuminate that the recovery rate is higher. Test results are seen in Table 8.

TABLE 8

Test results of sample injection recovery rate

| | Comparison item | Inspection results | | | | |
| --- | --- | --- | --- | --- | --- | --- |
| | | Peak 1 | Peak 2 | Peak 3 | Peak 4 | Peak 5 and 6 |
| Reference solution | Peak area | 120499 | 652794 | 19447 | 39935 | 429380 |
| | Retention time | 20.520 | 22.225 | 26.225 | 35.587 | 37.728 |
| Test solution | Peak area | 120173 | 644470 | 19338 | 39743 | 423083 |
| | Retention time | 21.027 | 22.708 | 26.730 | 36.327 | 38.335 | d. Reproducibility Test

Preparation of a reference solution: measuring a defined amount of ginkgoneolic acid control, precisely weighing, adding methanol to prepare a solution containing 5 μg of ginkgoneolic acid control each 1 ml as a reference solution; and moreover, measuring a defined amount of total ginkgoic acid control, precisely weighing, and adding methanol to prepare a solution containing 100 μg of total ginkgoic acid control each 1 ml as a location reference solution.

Preparation of a test solution: measuring 5 g of ginkgolides of the present invention, precisely weighing, in total 6 parts, respectively placing in a flask, adding 50 ml of n-hexane, refluxing for 2 h, cooling, filtering, washing a residue with a little n-hexane, combining a filtrate and a washing solution, drying by distillation on a water bath, dissolving a residue by adding methanol and diluting to 2 ml, and shaking well as a test solution.

Determination method: precisely drawing respectively 20 μl of test solution, reference solution and location reference solution, injecting in a liquid chromatograph, and recording chromatogram maps. Test results are seen in Table 9.

TABLE 9

Test results of reproducibility test

| Number | 1# | 2# | 3# | 4# | 5# | 6# |
|---|---|---|---|---|---|---|
| Inspection result of total ginkgoic acid | Not detected | Not detected | Not detected | Not detected | Not detected | Not detected |

Test results indicate that there is no ginkgolic acid in the ginkgolides of the present invention.

e. Recovery Rate Test

Preparation of a test solution: measuring 5 g of ginkgolides of the present invention, precisely weighing, in total 3 parts, respectively placing in a flask, respectively adding 1.6 ml, 2.0 ml and 2.4 ml of ginkgoneolic acid reference solution with a concentration of 3.04 μg/ml, respectively adding 50 ml of n-hexane, refluxing for 2 h, cooling, filtering, washing a residue with a little n-hexane, combining a filtrate and a washing solution, drying by distillation on a water bath, dissolving a residue by adding methanol and diluting to 2 ml, and shaking well as a test solution.

Preparation of a Reference Solution: The Same as that of the Reproducibility Test Determination method: precisely drawing respectively 20 μl of test solution and reference solution, injecting in a liquid chromatograph, and recording chromatogram maps. Each concentration is determined 3 times, in total 9 times. A recovery rate and an RSD value are calculated. Test results are seen in Table 10.

Test results indicate that the recovery rate is higher.

Example 9

Quality Control on Ginkgolides-Inspection of Fingerprint

Chromatographic condition and system suitability test: filling agent octadecyl silane bonded silica gel; mobile phase methanol-tetrahydrofuran-water (25:10:65); evaporative light-scattering detector, drift tube temperature 105° C.; carrier gas flow velocity 3.0 ml/min; and column temperature 40° C. A number of theoretical plates should not be less than 2500 calculated on a bilobalide peak. The separation degree of the bilobalide peak and the ginkgolide C peak should be greater than 1.5.

Preparation of a reference solution: respectively precisely measuring a defined amount of bilobalide control, ginkgolide A control, ginkgolide B control and ginkgolide C control, adding methanol to prepare a mixed solution containing 0.15 mg of bilobalide control, 0.12 mg of ginkgolide A control, 0.1 mg of ginkgolide B control and 0.1 mg of ginkgolide C control each 1 ml, and shaking well as a reference solution.

Preparation of a test solution: measuring 6 g of ginkgolides of the present invention, precisely weighing, placing in a 10 ml flask, dissolving by adding 1 ml of methanol, diluting to 2 ml by adding a mobile phase, and shaking well as a test solution.

Determination method: respectively precisely drawing respectively 20 μl of reference solution and test solution, injecting in a liquid chromatograph, and recording 60-min chromatogram maps.

According to a traditional Chinese medicine chromatographic fingerprint similarity evaluating system, the similarity of a test fingerprint and a control fingerprint is greater than 0.95.

The inventor researched and illuminated the above content of the present invention for proving the technical effect of the present invention. The following test is used for further illuminating and explaining the present invention, but not limiting the present invention.

Figure 5:
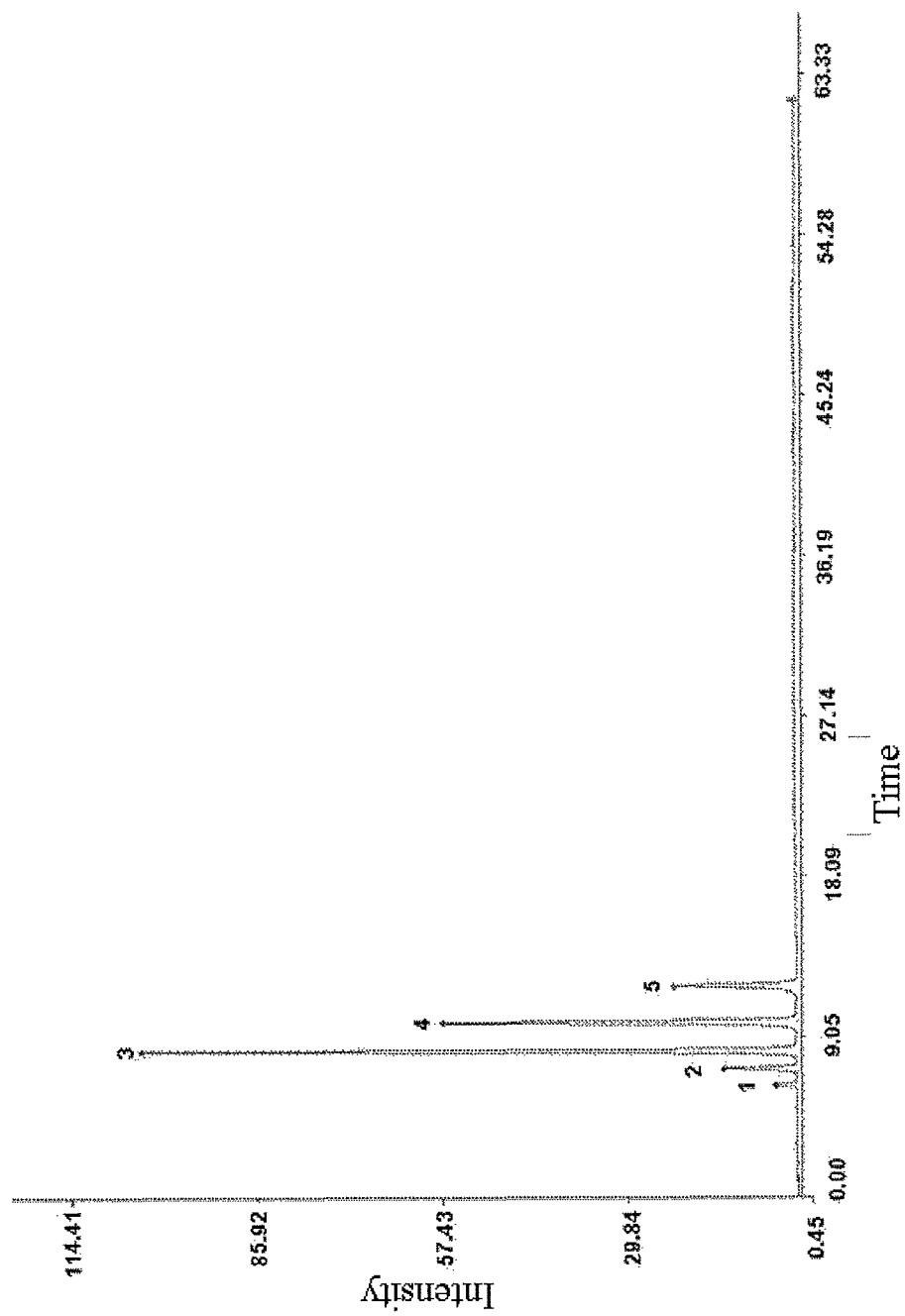
FIG. 5 is a control fingerprint of ginkgolides; In common peaks, peak 2: ginkgolide C; peak 3: bilobalide; peak 4: ginkgolide A; peak 5: ginkgolide B.

In a ginkgolide fingerprint, a peak 2 is ginkgolide C, a peak 3 is ginkgolide C, a peak 3 is bilobalide, a peak 4 is ginkgolide A, a peak 5 is ginkgolide B, four characteristic peaks of effective parts in this product may be in one-to-one correspondence in the fingerprint. A ginkgolide control fingerprint is seen in FIG. 5.

A traditional Chinese medicine chromatographic fingerprint similarity evaluating system as fingerprint software specified by the Chinese Pharmacopoeia Commission in 2004 is firstly adopted to respectively generate control fingerprints for 10 batches of ginkgolides, and the similarity of

TABLE 10

Table of test results of recovery rate test

| Number | 1# | 2# | 3# | 4# | 5# | 6# | 7# | 8# | 9# |
|---|---|---|---|---|---|---|---|---|---|
| Addition amount (μg) | | 4.864 | | | 6.080 | | | 7.26 | |
| Recovery amount (μg) | 5.291 | 4.811 | 5.090 | 6.454 | 6.374 | 6.389 | 7.563 | 7.446 | 7.452 |
| Recovery rate (%) | 108.77 | 98.90 | 104.66 | 106.16 | 104.84 | 105.09 | 103.66 | 102.06 | 103.38 |
| Average recovery rate (%) | | | | | 104.17 | | | | |
| RSD (%) | | | | | 2.62 | | | | | test fingerprints of different batches and the control fingerprint is calculated by using similarity software. Test results are seen in Table 11.

TABLE 11

Results of similarities of 10 batches of ginkgolides

| | Batch number | | | | |
|---|---|---|---|---|---|
| | 100401 | 100402 | 100403 | 100404 | 110101 |
| Similarity | 0.992 | 0.997 | 0.991 | 0.996 | 0.982 |

| | Batch number | | | | |
|---|---|---|---|---|---|
| | 110102 | 110103 | 110601 | 110602 | 110603 |
| Similarity | 0.999 | 0.997 | 0.992 | 0.993 | 0.989 |

The similarities of the fingerprints of 10 batches of ginkgolides are all greater than 0.95.

Example 10

Quality control in ginkgolides-determination of residual solvents (1) Ethanol, Ethyl Acetate and n-Hexane Preparation of a test solution: measuring about 0.1 g of ginkgolides of the present invention, precisely weighing, placing in a headspace bottle, precisely adding 5 ml of N,N-dimethylformamide to dissolve the ginkgolides, and sealing as a test solution.

Preparation of a reference solution, measuring a defined amount of ethanol, ethyl acetate and n-hexane, precisely weighing, quantitatively diluting with N,N-dimethylformamide into a solution respectively containing about 30 μg of ethanol, ethyl acetate and n-hexane each 1 ml, precisely weighing 5 ml of solution, placing in the headspace bottle, and sealing as a reference solution.

Determination method: with 6% cyanopropylphenyl-94% dimethyl polysiloxane (or with similar polarity) as a stationary liquid and an initial temperature of 50° C., maintaining for 3 min, raising the temperature to 160° C. at a rate of 40° C./min, maintaining for 3 min, wherein a temperature of an injection port is 200° C., a temperature of a detector is 250° C., an equilibrium temperature of the headspace bottle is 80° C., and an equilibrium time is 30 min; and measuring a reference solution for headspace injecting, wherein separation degrees among all ingredient peaks should meet the requirement; and then measuring a test solution and the reference solution for respectively headspace injection, recording chromatogram maps, and calculating in a peak area according to an external standard method.

The contents of ethanol and ethyl acetate are both less than 0.5%, and the content of n-hexane is less than 0.029%.

(2) Resin Residual Amount

Preparation of a reference solution: measuring a defined amount of N,N-dimethylacetamide, precisely weighing, preparing into a solution containing about 0.1 mg of N,N-dimethylacetamide each 1 ml with water, and shaking well as an internal standard solution; and precisely weighing a defined amount of caprolactam, and adding the internal standard solution to prepare a solution containing about 37.6 μg of caprolactam each 1 ml as a reference solution.

Preparation of a test solution: measuring about 2.5 g of ginkgolides of the present invention, precisely weighing, placing in a conical flask, adding 25 ml of n-hexane, refluxing for 2 h, cooling, filtering, washing a residue with a little n-hexane, combining a filtrate and a washing solution, drying by distillation on a 60° C. water bath, and adding 1 ml of internal standard solution to dissolve a residue as a test solution.

Determination method: with polyethylene glycol (PEG-20 M) (or polarity close) as a stationary liquid and an initial temperature of 100° C., maintaining for 2 min, raising the temperature to 160° C. at a rate of 40° C./min, maintaining for 3 min, raising the temperature to 220° C. at a rate of 40° C./min, maintaining for 7 min, wherein a temperature of an injection port is 240° C., and a temperature of a detector is 260° C.; and precisely measuring respectively 1 μl of reference solution and test solution, injecting in a gas chromatograph, and recording chromatogram maps; and calculating in a peak area according to an internal standard method, wherein the ratio of the peak area of the caprolactam in the test solution to the internal standard peak area is less than that of the peak area of the caprolactam in the reference solution to the internal standard peak area.

The caprolactam is not detected.

Example 11

Quality Control on Ginkgolides-Determination of Contents

Chromatographic condition and system suitability test: filling agent octadecyl silane bonded silica gel; mobile phase methanol-tetrahydrofuran-water (25:10:65); evaporative light-scattering detector, drift tube temperature 105° C.; carrier gas flow velocity 3.0 ml/min; and column temperature 40° C. A number of theoretical plates should not be less than 2500 calculated on a bilobalide peak. The separation degree of the bilobalide peak and the ginkgolide C peak should be greater than 1.5.

Preparation of a reference solution: respectively precisely measuring a defined amount of bilobalide control, ginkgolide A control, ginkgolide B control and ginkgolide C control, adding methanol to prepare a mixed solution containing 0.15 mg of bilobalide control, 0.12 mg of ginkgolide A control, 0.1 mg of ginkgolide B control and 0.1 mg of ginkgolide C control each 1 ml, and shaking well as a reference solution.

Preparation of a test solution: measuring 6 g of ginkgolides of the present invention, precisely weighing, placing in a 10 ml flask, dissolving by adding 1 ml of methanol, diluting to a scale by adding a mobile phase, and shaking well as a test solution.

Determination method: respectively precisely drawing respectively 10 μl of reference solution, 20 μl of reference solution and 10 to 20 μl of test solution, injecting in a liquid chromatograph, recording 60-min chromatogram maps, and respectively calculating contents of the bilobalide, the ginkgolide A, the ginkgolide B and the ginkgolide C by using an external standard two-point method logarithmic equation.

Calculated on a dry substance, the content of the bilobalide ($C_{15}H_{18}O_8$) is 42.5%, the content of the ginkgolide A ($C_{20}H_{24}O_9$) is 25.4%, the content of the ginkgolide B ($C_{20}H_{24}O_{10}$) is 18.7%, the content of the ginkgolide C ($C_{20}H_{24}O_{11}$) is 10.6%, and the sum of the bilobalide, the ginkgolide A, the ginkgolide B and the ginkgolide C is 97.2%.

Example 12

Quality Control on Ginkgolides-Inspection of Undue Toxicity

Preparation method of a test solution: measuring ginkgolides of the present invention, and adding a sodium chloride injection to prepare a solution containing 0.2 mg of ginkgolides each 1 ml.

Inspection method: taking 5 mice with weight of 17 to 20 g, and respectively injecting 0.5 ml of test solution in caudal veins of the mice, without death within 48 h.

Example 13

Quality Control on Ginkgolides-Inspection of Pyrogen

Preparation method of a test solution: measuring 10 mg of ginkgolides of the present invention, and adding in 50 ml of 0.9% sodium chloride injection, and shaking well.

Inspection method: taking 3 rabbits, after determining their normal body temperatures, within 15 min, slowly injecting the test solution in veins of ears according to an amount of 5 ml/kg each rabbit, determining body temperatures once every other 30 min, 6 times in total, wherein the body temperature rises are all lower than 0.6° C., and the sum of the body temperature rises of the 3 rabbits is lower than 1.3° C.

Example 14

Quality Control on Ginkgolides-Inspection of Related Substances

Prescription of an Injection

| | |
|---|---|
| Ginkgolides: in terms of terpene lactones | 1 to 10 mg/ml |
| Glycerinum | 0.2 to 0.5 ml/ml |
| Ethanol | 0.4 to 0.7 ml/ml |
| Injection water | 0 to 0.5 ml/ml |

A preparation method comprises:

a) preparing: mixing ethanol and glycerinum; adding the ginkgolides, dissolving; replenishing ethanol or injection water until full amount, and adjusting the pH value to 3.2 to 3.8 with a 5 to 10% citric acid solution or 1 to 10% hydrochloric acid solution;

b) filtering and getting rid of bacteria;

c) encapsulating;

d) sterilizing.

(1) Protein: measuring 2 ml of ginkgolide injection, adding water to prepare 50 ml of ginkgolide injection as a test solution; weighing about 50 mg of Coomassie brilliant blue G-250, dissolving in 25 ml of ethanol, then adding 50 ml of 85% (w/v) phosphoric acid, diluting to 500 ml by adding water, shaking well, filtering, precisely weighting 5 ml of filtrate, placing in a test tube, adding in 1 ml of test solution, shaking well, and placing for 3 min; preparing a blank solution by adopting the same method, determining the absorbance at a 595 nm wavelength, and the absorbance of the test solution is less than 0.05.

(2) Tannin: measuring 1 ml of protein inspection item test solution, adding 1 drop of dilute acetic acid, then adding 5 drops of gelatin sodium chloride test solution, shaking well, and placing for 10 min, without turbidity or precipitation.

(3) Resin: measuring 5 ml of protein inspection item test solution, adding 1 drop of hydrochloric acid, and placing for 30 min, without separating resinoids out.

(4) Oxalate: measuring 2 ml of protein inspection item test solution, adjusting the pH value to 1 to 2 with diluted hydrochloric acid, filtering, adjusting the pH value of a filtrate to 5 to 6 with ammonia water, adding 3 drops of 3% calcium chloride solution, and placing for 10 min, without turbidity or precipitation.

(5) Potassium ion: measuring 2 ml of protein inspection item test solution, placing in a 10 ml Nessler tube, adding 0.6 ml of alkaline formaldehyde solution, 2 drops of 3% EDTA solution and 0.5 ml of 3% sodium tetraphenylborate solution, diluting to 10 ml by adding water; and in addition, measuring 0.8 ml of standard potassium chloride solution, and testing by using the same method, wherein the turbidity of the test solution is not greater that of a reference solution.

Example 15

Quality Control on a Ginkgolide Injection-Inspection of Hemolysis and Coagulation Preparation of a test solution: measuring 6 ml of ginkgolide injection (prepared according to the example 14), adding in 100 ml of 0.9% sodium chloride injection, and shaking well.

Inspection method: taking 5 clean glass test tubes, numbering, wherein the tube I and II are test tubes, the tube III is a negative control tube, the tube IV is a positive control tube, the tube V is a test control tube; and sequentially adding a 2% red cell suspension, a 0.9% sodium chloride solution and distilled water according to Table 12, immediately placing in a calorstat of 37° C.±0.5° C. for incubation after uniformly mixing.

TABLE 12

Addition amounts in hemolysis and coagulation tests

| | Number of test tubes | | | | |
|---|---|---|---|---|---|
| | 1 | 2 | 3 | 4 | 5 |
| 2% red cell suspension/ml | 2.5 | 2.5 | 2.5 | 2.5 | |
| 0.9% sodium chloride solution/ml | 2.2 | 2.2 | 2.5 | | 4.7 |
| Distilled water/ml | | | | 2.5 | |
| Test solution/ml | 0.3 | 0.3 | | | 0.3 |

If the solution in the test tube is transparent and red and there are no cell residues or less red cell residues on the bottom, it indicates that the hemolysis occurs; and if all red cells sink and a supernate is colorless and transparent or supernate is colored and transparent, but no remarkable difference among the tubes 1, 2 and 5 is found by the naked eye, it indicate that no hemolysis occurs. It is observed that no hemolysis and coagulation are generated after 3 h.

Example 16

Quality Control on a Ginkgolide Injection-Inspection of Fingerprint

Chromatographic condition and system suitability test: filling agent octadecyl silane bonded silica gel; mobile phase methanol-tetrahydrofuran-water (25:10:65); evaporative light-scattering detector, drift tube temperature 105° C.; carrier gas flow velocity 3.0 ml/min; and column temperature 40° C. A number of theoretical plates should not be less than 2500 calculated on a bilobalide peak. The separation degree of the bilobalide peak and the ginkgolide C peak should be greater than 1.5.

Preparation of a reference solution: respectively precisely measuring a defined amount of bilobalide control, ginkgolide A control, ginkgolide B control and ginkgolide C control, adding methanol to prepare a mixed solution containing 0.15 mg of bilobalide control, 0.12 mg of ginkgolide A control, 0.1 mg of ginkgolide B control and 0.1 mg of ginkgolide C control each 1 ml, and shaking well as a reference solution.

Preparation of test solution: measuring the test solution in the item of the determination of contents.

Determination method: respectively precisely drawing respectively 20 μl of reference solution and test solution, injecting in a liquid chromatograph, and recording 60-min chromatogram maps.

According to a traditional Chinese medicine chromatographic fingerprint similarity evaluating system, the similarity of a test fingerprint and a control fingerprint is greater than 0.95.

Example 17

Quality Control on a Ginkgolide Injection-Determination of Contents

Chromatographic condition and system suitability test: filling agent octadecyl silane bonded silica gel; mobile phase methanol-tetrahydrofuran-water (25:10:65); evaporative light-scattering detector, drift tube temperature 105° C.; carrier gas flow velocity 3.0 ml/min; and column temperature 40° C. A number of theoretical plates should not be less than 2500 calculated on a bilobalide peak. The separation degree of the bilobalide peak and the ginkgolide C peak should be greater than 1.5.

Preparation of a reference solution: respectively precisely measuring a defined amount of bilobalide control, ginkgolide A control, ginkgolide B control and ginkgolide C control, adding methanol to prepare a mixed solution containing 0.15 mg of bilobalide control, 0.12 mg of ginkgolide A control, 0.1 mg of ginkgolide B control and 0.1 mg of ginkgolide C control each 1 ml, and shaking well as a reference solution.

Preparation of a test solution: precisely measuring 1 ml of ginkgolide injection (prepared according to the example 14), adding 14 ml of phosphate buffered solution (pH 6.5), shaking well, applying to a Extrelut-20 column, adsorbing for 15 min, eluting with 100 ml of ethyl acetate, collecting an eluant, drying by distillation on a water bath, dissolving a residue with a mobile phase and transferring to a 10 ml measuring flask, diluting to a scale by adding the mobile phase, shaking well, and filtering with a 0.45 μm millipore filter membrane as a test solution.

Determination method: respectively precisely drawing respectively 10 μl of reference solution, 20 μl of reference solution and 15 μl of test solution, injecting in a liquid chromatograph, recording chromatogram maps, and respectively calculating contents of the bilobalide, the ginkgolide A, the ginkgolide B and the ginkgolide C by using an external standard two-point method logarithmic equation.

Each 1 ml of ginkgolide injection contains 5.15 mg of ginkgo terpene lactones.

Each 1 ml of ginkgolide injection contains 1 to 10 mg, preferably 4.25 to 5.75 mg of ginkgo terpene lactones in the terms of the total amount of the bilobalide ($C_{15}H_{18}O_8$), the ginkgolide A ($C_{20}H_{24}O_9$), the ginkgolide B ($C_{20}H_{24}O_{10}$), and the ginkgolide C ($C_{20}H_{24}O_{11}$).

What is claimed is:

1. A method for extracting and separating ginkgolides, comprising:
A. extracting:
crushing ginkgo leaves, adding an organic solvent for extraction to produce an extracted solution,
concentrating the extracted solution to produce a concentrated extracted solution,
adding an anti-oxidization protection agent to the concentrated extracted solution, adjusting a pH to 4 to 5 with a pH adjusting agent, which is followed by concentrating and refrigerating to form a refrigerated concentrated solution;
wherein in the step A, the organic solvent for extraction is ethanol, acetone, or ethyl acetate, with a concentration of 50 to 80% v/v and an amount in liters that is in a range of from 5 to 12 times a number equal to a mass in kilograms of the ginkgo leaves;
B. further extracting:
extracting the refrigerated concentrated solution 2 to 3 times with n-hexane or petroleum ether firstly to produce a first aqueous phase and a first organic extracting phase,
extracting the first aqueous phase 4 to 5 times with a lipid-soluble solvent to produce a second aqueous phase and a second organic extracting phase,
extracting the second aqueous phase 4 to 5 times with a water saturated sec-butyl alcohol-ethyl acetate mixed solvent or water saturated n-butyl-ethyl acetate mixed solvent to produce a third aqueous phase and a third organic extracting phase,
combining the second and the third organic phase extracted solutions, and concentrating under reduced pressure to produce a extracted concentrated solution;
C. passing through a column:
passing the extracted concentrated solution through a polyamide resin column, sequentially eluting with 15 BV of water, 3 to 5 BV of 20% to 40% v/v ethanol and 2 to 3 BV of 60% to 90% v/v ethanol, controlling a flow velocity of an eluant to 2 to 3 BV/h;
concentrating the eluant under reduced pressure, and drying to produce a dry substance;
D. separating crystals out:
adding the dry substance to boiling water, dissolving by agitating, cooling, extracting a supernate 4 to 5 times with ethyl acetate, ethyl formate or acetone in a volume equal to that of the supernate, combining extracted solutions, concentrating under reduced pressure, drying by distillation, adding an amount of 30% to 50% v/v ethanol in liters that in a range of from 5 to 8 times a number equal to a mass in kilograms of the dried substance, dissolving by heating and agitating, filtering, refrigerating, separating crystals out, filtering to obtain a filtrate I for later use, washing the crystals with 30% to 50% v/v ethanol, and drying under reduced pressure to obtain crystals I;
concentrating the filtrate I until the alcohol content is 10 to 30% v/v, refrigerating, separating crystals out, filtering to obtain a filtrate II for later use; and washing with 30 to 50% v/v ethanol, and drying under reduced pressure to obtain crystals II;
concentrating the filtrate II, adding 0.1% to 0.5% active carbon for adsorption, filtering to obtain a filtrate, concentrating the filtrate until the alcohol content is 10% to 30% v/v, refrigerating, separating crystals out, filtering to obtain a filtrate III for later use, washing the crystals with 30% to 50% v/v ethanol, and drying under reduced pressure to obtain crystals III;
concentrating the filtrate III, passing through an active-carbon-silica gel column, eluting with 30% to 50% v/v ethanol firstly, then eluting with 70% to 90% v/v ethanol, collecting eluants, concentrating until the alcohol content is 10% to 30% v/v, refrigerating and separating crystals out, filtering the crystals out to obtain a filtrate IV for later use; and washing the crystals with 30% ethanol, and drying under reduced pressure to obtain crystals IV;

concentrating the filtrate IV, refrigerating, separating crystals out, filtering, washing the crystals with 30% v/v ethanol, and drying under reduced pressure to obtain crystals V; and E. mixing the crystals:

uniformly mixing the crystals I, II, III, IV and V, and crushing to obtain the ginkgolides.

2. The method for extracting and separating ginkgolides according to claim 1, wherein a manner of the extracting in the A is reflux extraction or decoction extraction.

3. The method for extracting and separating ginkgolides according to claim 2, wherein the reflux extraction adopts ethanol, acetone or ethyl acetate for extraction, wherein concentrations of different extracting solvents and extraction conditions are as follows:

ethanol: concentration 50% to 80% v/v, extraction temperature 75 to 85° C., extraction times 2 to 3 times with 1 to 2 h a time; acetone: concentration 50% to 80% v/v, extraction temperature 45 to 55° C., extraction times 2 to 3 times with 1 to 2 h a time; ethyl acetate: concentration 50% to 80% v/v, extraction temperature 55 to 65° C., extraction times 2 to 3 times with 1 to 2 h a time.

4. The method for extracting and separating ginkgolides according to claim 3, wherein the reflux extraction adopts ethanol, acetone or ethyl acetate for extraction, wherein concentrations of different extracting solvents and extraction conditions are as follows:

ethanol: concentration 65% v/v, extraction temperature 75 to 85° C., extraction times 3 times with 1.5 h a time; acetone: concentration 50% v/v, extraction temperature 45 to 55° C., extraction times 3 times with 1.5 h a time; ethyl acetate: concentration 60% v/v, extraction temperature 55 to 65° C., extraction times 3 times with 1.5 h a time.

5. The method for extracting and separating ginkgolides according to claim 2, wherein the decoction extraction adopts ethanol, acetone or ethyl acetate for extraction, wherein concentrations of different extracting solvents and extraction conditions are as follows:

ethanol: concentration 50% to 80% v/v, extraction temperature 80 to 90° C., extraction times 2 to 3 times with 1 to 2 h a time; acetone: concentration 50% to 80% v/v, extraction temperature 50 to 60° C., extraction times 2 to 3 times with 1 to 2 h a time; ethyl acetate: concentration 50% to 80% v/v, extraction temperature 60 to 65° C., extraction times 2 to 3 times with 1 to 2 h a time.

6. The method for extracting and separating ginkgolides according to claim 5, wherein the decoction extraction adopts ethanol, acetone or ethyl acetate for extraction, wherein concentrations of different extracting solvents and extraction conditions are as follows:

ethanol: concentration 65% v/v, extraction temperature 80 to 90° C., extraction times 3 times with 1.5 h a time; acetone: concentration 50% v/v, extraction temperature 50 to 60° C., extraction times 3 times with 1.5 h a time; ethyl acetate: concentration 60% v/v, extraction temperature 60 to 65° C., extraction times 3 times with 1.5 h a time.

7. The method for extracting and separating ginkgolides according to claim 1, wherein the anti-oxidization protection agent in the step A is neutral amino acid.

8. The method for extracting and separating ginkgolides according to claim 1, wherein the anti-oxidization protection agent in the step A is at least one of serine, methionine, asparagine or threonine.

9. The method for extracting and separating ginkgolides according to claim 1, wherein the anti-oxidization protection agent in the step A is methionine.

10. The method for extracting and separating ginkgolides according to claim 1, wherein the pH adjusting agent in the step A is organic weak acid.

11. The method for extracting and separating ginkgolides according to claim 1, wherein the pH adjusting agent in the step A is at least one of citric acid, malic acid or sorbic acid.

12. The method for extracting and separating ginkgolides according to claim 1, wherein the pH adjusting agent in the step A is citric acid.

13. The method for extracting and separating ginkgolides according to claim 1, wherein the lipid-soluble solvent in the step B is at least one ethyl acetate, ethyl formate, acetone or butanone.

14. The method for extracting and separating ginkgolides according to claim 1, wherein the particle size of polyamide resin in the polyamide resin column in the step C of passing through the polyamide resin column is 30 to 60 mu.

15. The method for extracting and separating ginkgolides according to claim 1, wherein the volume ratio of active carbon and silica gel in the active carbon-silica-gel column in the step D of separating crystals out is 1:1 to 1:3.

* * * * *